(12) United States Patent
Zhang et al.

(10) Patent No.: US 11,401,303 B2
(45) Date of Patent: Aug. 2, 2022

(54) SYNTHETIC PEPTIDE BRAP AND APPLICATION IN PREPARATION OF ANTI-INFLAMMATORY DRUG FOR COVID-19 THEREOF

(71) Applicant: TAIAN CITY QIHANG BIOTECHNOLOGY CO., Shandong (CN)

(72) Inventors: Wanqin Zhang, Shandong (CN); Yintian Li, Feicheng (CN); Xuewen Ji, Shandong (CN); Limei Zhao, Shandong (CN)

(73) Assignee: TAIAN CITY QIHANG BIOTECHNOLOGY CO., Feicheng (CN)

( * ) Notice: Subject to any disclaimer, the term of this patent is extended or adjusted under 35 U.S.C. 154(b) by 0 days.

(21) Appl. No.: 17/310,121

(22) PCT Filed: Mar. 3, 2020

(86) PCT No.: PCT/CN2020/100629
§ 371 (c)(1),
(2) Date: Jul. 16, 2021

(87) PCT Pub. No.: WO2021/253523
PCT Pub. Date: Dec. 23, 2021

(65) Prior Publication Data
US 2022/0144891 A1    May 12, 2022

(30) Foreign Application Priority Data
Jun. 15, 2020  (CN) .......................... 202010546684.0

(51) Int. Cl.
| | |
|---|---|
| *C07K 7/06* | (2006.01) |
| *A61P 11/00* | (2006.01) |
| *A61K 38/00* | (2006.01) |
| *A61P 37/08* | (2006.01) |
| *A61P 37/06* | (2006.01) |

(52) U.S. Cl.
CPC ................ *C07K 7/06* (2013.01); *A61P 11/00* (2018.01); *A61P 37/06* (2018.01); *A61P 37/08* (2018.01); *A61K 38/00* (2013.01)

(58) Field of Classification Search
CPC ............ C07K 7/06; A61P 11/00; A61K 38/00
See application file for complete search history.

(56) References Cited

U.S. PATENT DOCUMENTS

2012/0219578 A1* 8/2012 Galeotti ................. C07K 14/22
424/190.1
2018/0088121 A1* 3/2018 Gerhard ............. C07K 14/4748

FOREIGN PATENT DOCUMENTS

| CN | 105228623 A | 1/2016 |
| CN | 109232718 A | 1/2019 |
| WO | 2005042027 A2 | 5/2005 |

OTHER PUBLICATIONS

Chida-Nagai et al., 2019, Role of BRAC1-associated protein (BRAP) variant in childhood pulmonary arterial hypertension, PLoS ONE, 14(1): e0211450 (16 pages).*
Landgraf, R. Gama et al.; Modulation of allergic and immune complex-induced lung inflammation by bradykinin receptor antagonists, Inflammation Research, Dec. 31, 2004, vol. 53, pp. 78-83.
Wang, Ruixue et al.; Sybthesis of Novel Bradykinin B2 Receptor Antagonists; Full-text database of China's outstanding master's thesis Engineering Technology Series I, Sep. 15, 2012, vol. 9, B016-115.
Dai, Hongliang et al.; Role of Bradykinin in the Pathogenesis of Allergic Diseases; Chinese Journal of Clinical Immunity and Allergy, Dec. 31, 2014, pp. 306-310.
Regoli, Domenico et al.; New selective bradykinin receptor antagonists and bradykinin B2 receptor characterization; TIPS, Apr. 30, 1990, vol. 11, pp. 156-161.
Zhang, Qingzhu et al.; Research progress of bradykinin receptor and its antagonists ; Foreign medicine-synthetic drugs, biochemical drugs, preparations Dec. 31, 1992, vol. 1, No. 13, pp. 22-23.

* cited by examiner

*Primary Examiner* — Amber D Steele
(74) *Attorney, Agent, or Firm* — Novick, Kim & Lee, PLLC; Allen Xue

(57) ABSTRACT

A synthetic peptide brap can be used in preparing an anti-inflammatory drug for COVID-19. The amino acid sequence of a synthetic peptide brap is as shown in SEQ ID No: 1. The synthetic bradykinin receptor antagonism peptide (brap) has significant target-docking and inhibiting effects on G-protein-coupled bradykinin B1 and B2 receptors. The intranasal administration of brap has local effects on allergic nasal inflammation, and has systemic pharmacodynamic effect on pulmonary leakage, lung injury and LPS-induced cytokine storm. The intravenous injection of brap has an obvious inhibiting effect on the excessive inflammation, oxidative stress response and serious lung injury emerging in LPS-induced mice; and has an obvious inhibiting effect on the excessive release of proinflammatory factors IL-6 and TNF-α, overexpression of IL-6 mRNA, and massive generation of reactive oxygen species (ROS) in the LPS-induced inflammatory factor storm.

10 Claims, 21 Drawing Sheets
Specification includes a Sequence Listing.

```
                        SEQUENCE LISTING

<160> NUMBER OF SEQ ID NOS: 7

<210> SEQ ID NO 1
<211> LENGTH: 10
<212> TYPE: PRT
<213> ORGANISM: Artificial Sequence
<220> FEATURE:
<223> OTHER INFORMATION: synthesized

<400> SEQUENCE: 1

Arg Val Leu Asn Gly Pro Glu Ala Pro Ala
1               5                   10

<210> SEQ ID NO 2
<211> LENGTH: 15
<212> TYPE: PRT
<213> ORGANISM: Artificial Sequence
<220> FEATURE:
<223> OTHER INFORMATION: synthesized

<400> SEQUENCE: 2

Arg Val Leu Asn Gly Pro Glu Glu Glu Ala Ala Ala Pro Ala Glu
1               5                   10                  15

<210> SEQ ID NO 3
<211> LENGTH: 20
<212> TYPE: DNA
<213> ORGANISM: Artificial Sequence
<220> FEATURE:
<223> OTHER INFORMATION: synthesized
```

```
<400> SEQUENCE: 3
ccaccgggaa cgaaagagaa                                                  20

<210> SEQ ID NO 4
<211> LENGTH: 20
<212> TYPE: DNA
<213> ORGANISM: Artificial Sequence
<220> FEATURE:
<223> OTHER INFORMATION: synthesized

<400> SEQUENCE: 4
gagaaggcaa ctggaccgaa                                                  20

<210> SEQ ID NO 5
<211> LENGTH: 20
<212> TYPE: DNA
<213> ORGANISM: Artificial Sequence
<220> FEATURE:
<223> OTHER INFORMATION: synthesized

<400> SEQUENCE: 5
gacagccgca tcttcttgtg                                                  20

<210> SEQ ID NO 6
<211> LENGTH: 20
<212> TYPE: DNA
<213> ORGANISM: Artificial Sequence
<220> FEATURE:
<223> OTHER INFORMATION: synthesized

<400> SEQUENCE: 6
aatccgttca caccgacctt                                                  20

<210> SEQ ID NO 7
<211> LENGTH: 353
<212> TYPE: PRT
<213> ORGANISM: Artificial Sequence
<220> FEATURE:
<223> OTHER INFORMATION: synthesized

<400> SEQUENCE: 7
```

| Met | Ala | Ser | Ser | Trp | Pro | Pro | Leu | Glu | Leu | Gln | Ser | Ser | Asn | Gln | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gln | Leu | Phe | Pro | Gln | Asn | Ala | Thr | Ala | Cys | Asp | Asn | Ala | Pro | Glu | Ala |
|     |     |     | 20  |     |     |     |     | 25  |     |     |     |     | 30  |     |     |

| Trp | Asp | Leu | Leu | His | Arg | Val | Leu | Pro | Thr | Phe | Ile | Ile | Ser | Ile | Cys |
|     |     |     | 35  |     |     |     |     | 40  |     |     |     |     | 45  |     |     |

| Phe | Phe | Gly | Leu | Leu | Gly | Asn | Leu | Phe | Val | Leu | Val | Phe | Leu | Leu |
|     | 50  |     |     |     |     | 55  |     |     |     |     | 60  |     |     |     |

| Pro | Arg | Arg | Gln | Leu | Asn | Val | Ala | Glu | Ile | Tyr | Leu | Ala | Asn | Leu | Ala |
| 65  |     |     |     |     | 70  |     |     |     |     | 75  |     |     |     |     | 80  |

| Ala | Ser | Asp | Leu | Val | Phe | Val | Leu | Gly | Leu | Pro | Phe | Trp | Ala | Glu | Asn |
|     |     |     |     | 85  |     |     |     |     | 90  |     |     |     |     | 95  |     |

| Ile | Trp | Asn | Gln | Phe | Asn | Trp | Pro | Phe | Gly | Ala | Leu | Leu | Cys | Arg | Val |
|     |     |     | 100 |     |     |     |     | 105 |     |     |     |     | 110 |     |     |

| Ile | Asn | Gly | Val | Ile | Lys | Ala | Asn | Leu | Phe | Ile | Ser | Ile | Phe | Leu | Val |
|     |     |     | 115 |     |     |     |     | 120 |     |     |     |     | 125 |     |     |

| Val | Ala | Ile | Ser | Gln | Asp | Arg | Tyr | Arg | Val | Leu | Val | His | Pro | Met | Ala |
|     | 130 |     |     |     |     | 135 |     |     |     |     | 140 |     |     |     |     |

| Ser | Arg | Arg | Gln | Gln | Arg | Arg | Gln | Ala | Arg | Val | Thr | Cys | Val | Leu |
| 145 |     |     |     |     | 150 |     |     |     |     | 155 |     |     |     |     | 160 |

-continued

```
Ile Trp Val Val Gly Gly Leu Leu Ser Ile Pro Thr Phe Leu Leu Arg
            165             170             175

Ser Ile Gln Ala Val Pro Asp Leu Asn Ile Thr Ala Cys Ile Leu Leu
            180             185             190

Leu Pro His Glu Ala Trp His Phe Ala Arg Ile Val Glu Leu Asn Ile
            195             200             205

Leu Gly Phe Leu Leu Pro Leu Ala Ala Ile Val Phe Phe Asn Tyr His
            210             215             220

Ile Leu Ala Ser Leu Arg Thr Arg Glu Glu Val Ser Arg Thr Arg Cys
225             230             235             240

Gly Gly Arg Lys Asp Ser Lys Thr Thr Ala Leu Ile Leu Thr Leu Val
            245             250             255

Val Ala Phe Leu Val Cys Trp Ala Pro Tyr His Phe Phe Ala Phe Leu
            260             265             270

Glu Phe Leu Phe Gln Val Gln Ala Val Arg Gly Cys Phe Trp Glu Asp
            275             280             285

Phe Ile Asp Leu Gly Leu Gln Leu Ala Asn Phe Phe Ala Phe Thr Asn
            290             295             300

Ser Ser Leu Asn Pro Val Ile Tyr Val Phe Val Gly Arg Leu Phe Arg
305             310             315             320

Thr Lys Val Trp Glu Leu Tyr Lys Gln Cys Thr Pro Lys Ser Leu Ala
            325             330             335

Pro Ile Ser Ser Ser His Arg Lys Glu Ile Phe Gln Leu Phe Trp Arg
            340             345             350

Asn
```

SYNTHETIC PEPTIDE BRAP AND APPLICATION IN PREPARATION OF ANTI-INFLAMMATORY DRUG FOR COVID-19 THEREOF

INCORPORATION OF SEQUENCE LISTING

This application contains a sequence listing submitted in Computer Readable Form (CRF). The CFR file containing the sequence listing entitled "PA128-0109_ST25.txt", which was created on Jul. 16, 2021, and is 4,638 bytes in size. The information in the sequence listing is incorporated herein by reference in its entirety.

TECHNICAL FIELD

The present invention belongs to the technical field of biomedicines, and relates to a synthetic peptide brap (bradykinin receptor antagonism peptides) and application in the preparation of anti-acute lung injury drug thereof, in particular an anti-inflammatory drug for novel coronavirus pneumonia (NCP), also named COVID-19.

BACKGROUND

Severe COVID-19 is threatening the life of our human being seriously. Scientific workers have found that the target corresponding to novel coronavirus is an angiotensin converting enzyme II (ACE2). When the S protein of the virus specifically binds to ACE2 on the cell, the virus enters the cell. ACE2 is the target (i.e., cell receptor) of a cell infected with novel coronavirus, and is also a key factor to cause the pathogenesis of lung injury after infection. The virus duplicates in the infected cell and causes a reduced ACE2 level; ACE2 is an important member in Renin-Angiotensin-Aldosterone System (RAAS) and Kallikrein-Kinin System (KKS). In RAAS system, the decrease of ACE2 level results in the imbalance of ACE2 and ACE (angiotensin converting enzyme), and ACE is relatively enhanced to cause an increase of Ang II level, which excessively activates an AT1a receptor of lung, leading to enhanced capillary permeability of the lung followed by pulmonary edema, thereby aggravating the inflammatory of the lung. In KKS system, Des-Arg bradykinin is an agonist of the B1 receptor. ACE2 can degrade the Des-Arg bradykinin in the Des-Arg bradykinin-B1 receptor pathway into an inactivated peptide. The decrease of ACE2 level results in activation of the Des-Arg bradykinin-B1 receptor pathway. The activation of the B1 receptor has the effect of promoting inflammation.

After virus infection, the infected cell produces inflammatory factors which resist virus and control the natural immune response. But when the virus duplicates massively in the infected cell, the immune system will be excessively activated, resulting in an increase of proinflammatory factors, such as IL-6, TNF-α, and IFN-γ. The proinflammatory factors can activate and recruit other immune cells to secrete more cytokines, thereby bringing systemic immuno-inflammatory responses rapidly to cause multiple organ failure. The pathogenesis of the cytokine storm caused by COVID-19 is unclear currently. There is evidence to show that the severity of the severe COVID-19 is closely related to the increase level of the proinflammatory factor IL-6. The increase of IL-6 is an indicator of poor prognosis. It is widely believed by experts that the effect of IL-6 inhibitor is worthy of the wait.

SUMMARY OF THE INVENTION

The present invention provides a synthetic peptide brap, having an amino acid sequence of SEQ ID No: 1.

The present invention further provides applications of the synthetic peptide brap in any one of the following (1) to (4): (1) preparation of a drug for inhibiting G-protein-coupled bradykinin B1 and B2 receptors; (2) preparation of an anti-acute lung injury drug; (3) preparation of an anti-inflammatory drug for COVID-19; and (4) preparation of an anti-allergic rhinitis drug.

Further, in the above technical solution, the drug in any one of application (1) to (4) is administered intravenously or intranasally.

The application of the present invention has low toxicity, and no toxicity is found in a limit test on intravenous injection of 2000 mg/kg BW dose level.

The synthetic peptide brap disclosed in the present invention is a 10-peptide compound (FIGS. 1A-1B) composed of 8 amino acids, having an amino acid sequence as shown in SEQ ID No: 1. The synthetic peptide brap can be industrially synthesized with a solid-phase chemical synthesis technology, having a purity of ≥99.5 (FIGS. 2-3). No toxicity is found in a limit test on intravenous injection of 2000 mg/kg BW dose level (Table 2). The relationship between brap and acute lung injury (ALI), especially COVID-19 pneumonia, has been found recently. Acute lung injury is a substantive diffuse-lung respiratory disease featured by leakage and inflammation due to the injury of alveolar epithelial cells and capillary endothelial cells caused by various factors. After novel coronavirus enters the human body, the pathogenic process to lung includes the injury caused by pathophysiologic reaction of the virus to cells (pathophysiologic reaction featured by leakage and inflammation) and body immunopathological reaction (the virus duplicates in the infected cell to cause the release of inflammatory factors; and the virus duplicates massively to cause the excessive activation of the immunity system, resulting in cytokine storm).

The lung injury caused by pathophysiologic reaction of the virus to cells is because the target ACE2 corresponding to novel coronavirus belongs to KKS and RAAS systems simultaneously. KKS and RAAS systems are activated simultaneously when virus infection causes the decrease of ACE2 level. In RAAS system, the decrease of ACE2 level results in the imbalance of ACE2 and ACE, and ACE is relatively enhanced to cause an increase of the Ang II level and excessively activates the AT1a receptor of lung, leading to enhanced pulmonary capillary permeability and pulmonary capillary leakage. ACE2 also belongs to KKS, and Des-Arg bradykinin is a B1 receptor agonist of the Bradykinin (BK). ACE2 can degrade the Des-Arg bradykinin into an inactivated peptide. When the infection of novel coronavirus causes a decrease of ACE2 level in the infected cells, the Des-Arg bradykinin-B1 receptor pathway is activated. BK binds to a receptor to exert biological effects. BK receptor is a kind of G protein coupled receptor (GPCR), including type B1 and type B2. B1 receptor of BK is inductive expression that tissue injury and inflammatory response can induce the B1 receptor for expression. After the B1 receptor is activated, proinflammatory cytokines are released to enhance neutrophil leakage and activate neutrophil to produce excessive inflammatory mediators and reactive oxygen species, thus participating in the inflammatory response of the injured parts, thereby expanding pulmonary inflammation and injury. Activation of B2 receptor can obviously enhance microvascular permeability, and a large amount of plasma components are leaked to cause pulmonary leakage. The present invention proves that the synthetic peptide brap has obvious target docking and inhibiting effects with the G-protein-coupled bradykinin B2 receptor.

The synthetic peptide brap is docked with the target bradykinin B2 receptor thereof and distributed into an open pocket composed of transmembrane helices of B2 receptor protein; No. 1 residue points to the outside of the pocket and No. 10 residue is located at the bottom of the pocket. By the analysis on the binding site of brap to the B2 receptor, 10 residues are docked with the B2 receptor; and energy contribution of each residue of a small peptide is calculated (FIG. 4). The present invention proves that brap has an obvious inhibitory effect on the B2 receptor functionally (FIGS. 5A-5B). The present invention proves that the synthetic peptide brap (50 µl/side) administered in bilateral nasal cavities has obvious inhibitory effects (P<0.01) both on rat allergic nasal inflammation and BK-induced pulmonary microvascular leakage in guinea pig, and have dose-response relationships (FIGS. 6A-6B and FIGS. 7A-7B). In the present invention, MDock-PeP is also used for the docking of a brap structure to B1R (B1 receptor) of BK. Two different methods are used for modeling two B1 receptor structures docking with the brap respectively and obtain 2 docking results; and further analyze the interacting residues between the B1 receptor (B1R) and the synthetic peptide (the ligand). The present invention proves that brap is bonded into the receptor pocket in U-shaped (FIG. 8). An intracellular calcium ion fluorescent technique is used to detect an influence of brap on the functional activity of Bradykinin B1 Receptor, which prove that brap has an obvious inhibiting effect on the B1 receptor and can reduce the excessive activation of the B1 receptor (FIGS. 9A-9B). The incubation period of COVID-19 is just the occurrence and development stages of the pathophysiological process of pulmonary leakage and inflammation caused by the reduced ACE2 level after the post-infection stage of the virus. The period from the incubation period to definite diagnosis is the prime time to treat lung injury of novel coronavirus pneumonia. By the antagonistic effects to G-protein-coupled bradykinin B1 and B2 receptors, the brap effectively block out the pathological reaction during the occurrence of novel coronavirus pneumonia caused by the reduced ACE2, and even to obviously relieve the enhanced pulmonary vascular permeability and pulmonary leakage of guinea pig caused by bradykinin by simple intranasal administration.

However, a human body eliminates the virus indeed by killing the virus with our body's immune system. In early stage of infection, an S protein of novel coronavirus specifically binds to ACE2 on the cells; and when the virus begins to duplicate in the cells, the body's immune system is stimulated and the infected cells produce inflammatory cytokines, having antiviral and immunomodulatory effects. In later stage of infection, when the virus duplicates in the infected cells massively, the body is induced to excessive immune response, resulting in cytokine storm, thereby the pulmonary immune cells are activated excessively to generate a large number of cytokines.

Lipopolysaccharide (LPS) is a kind of cell wall constituent of Gram negative bacteria, and also a major component of bacterial endotoxin. LPS can activate mononuclear phagocyte system to promote the release of proinflammatory cytokines, such as tumor necrosis factor (TNF-α) and interleukin 6 (IL-6), and to activate more production of neutrophil, inflammatory media and reactive oxygen species (ROS). Further, in the present invention, LPS is used to induce excessive inflammation, oxidative stress response and severe cytokine storm process in mice. Results show that mice both in LPS model group and model administration group are at state near death after 6 h, when being intraperitoneally injected with LPS (5 mg/kg i.p.). The mice suffer energielos, polypnea, shrugging hair, loose stools, periocular secreta, lacrimation and other systemic involvement symptoms of multiple organs. The contents of bacterial endotoxin in serum, IL-6, TNF-α and the expression of lung tissue IL-6 mRNA increase remarkably, and the pulmonary ROS content increases remarkably as well (FIGS. 10-15), and mice suffer the pathological manifestations of lung injury below: thickened pulmonary septum, inflammatory cell infiltration, focal fusion of pulmonary septum (FIGS. 16A-16H).

The brap intravenous injection obviously decreases the endotoxin level in blood (FIG. 10), obviously decreases the overexpression of IL-6 mRNA in lung tissues (FIG. 11), obviously decreases the levels of proinflammatory cytokines IL-6 and TNF-α in blood (FIGS. 12A-12C and FIGS. 13A-13C), obviously decreases the overly increased ROS content in lung tissues (FIGS. 14A-14G and FIG. 15), and obviously relieves the pathological manifestations of lung injury (FIGS. 16A-16H). Meanwhile, the present invention shows that the intranasal administration of brap has the pharmacodynamic effect of obviously reducing the overexpression of IL-6 mRNA in lung tissues (FIG. 11), reducing the level of proinflammatory cytokines IL-6 and TNF-α in blood (FIGS. 12A-12C and FIGS. 13A-13C), reducing the overly increased ROS content in lung tissues (FIGS. 14A-14G and FIG. 15), and obviously relieving the interstitial inflammation of lung injury, thickened pulmonary septum, large number of inflammatory cell infiltration and other pathological changes (FIGS. 16A-16H).

It has been reported that severe novel coronavirus pneumonia patients are prone to cytokine storm (i.e., inflammation storm). Scientific workers have found that IL-6 is a kind of important inflammatory factor and is an important passage to induce inflammation storm. The present invention shows that both intravenous and intranasal administration of brap can obviously decrease the expression of excessively-elevated IL-6 mRNA in lung tissues of LPS-induced Balbc mice. Further, the present invention shows that the brap has an obvious inhibitory effect (P<0.01) both on rat allergic nasal inflammation and BK-induced cavy pulmonary capillary leakage, and there are dose-response relationships (FIGS. 6A-6B and FIGS. 7A-7B). Intranasal administration can render the drug to enter blood circulation rapidly to obviously relieve pulmonary leakage (FIGS. 7A-7B) and lung injury (FIG. 15) rapidly, and can obviously inhibit the expression of inflammatory factor IL-6 mRNA in lung tissues (FIG. 11). The present invention provides experimental evidence that the intranasal administration of brap also can be used for preventing and treating acute lung injury. The brap is a kind of small peptide synthesized by a polypeptide solid-phase synthesis technique, purified by high performance liquid chromatography (HPLC) and identified by mass spectrometry, which provides quantitative data for drug preparation, structure confirmation, quality research and other aspects of the brap. Due to brap has blocking effects both on B1 and B2 receptors of G-protein-coupled BK, in the occurrence and development stages of novel coronavirus pneumonia, brap has a significant inhibiting effect on pulmonary leakage; in the inflammation progressing stage, brap has a significant inhibiting effect on excessive inflammation and oxidative stress response, and has a significant protective effect on lung tissue injury; if the condition develops to a critical inflammation storm stage, the brap can obviously inhibit the over-activated immuno-inflammatory responses and decrease the excessive activation of the immunity system. Moreover, according to the disease progression, different mode of intranasal or intravenous administration can be given. At present, a drug clinically used in anti-inflammatory treatment mainly includes glucocorticoid, but glucocorticoid has obvious side effect in the prior art, there is no application of a similar compound in anti-inflammatory drug for novel coronavirus pneumonia.

BRIEF DESCRIPTION OF THE DRAWINGS

FIG. 1A shows a graph of the amino acid composition of the synthetic peptide brap drawn by an amino acid analyzer; FIG. 1B is a diagram showing amino acid components of a standard used in amino acid detection of the synthetic peptide brap.

FIG. 5A is the dose-response curve of the positive control bradykinin B2 receptor inhibitor HOE-140 of the synthetic peptide brap; FIG. 5B is the dose-response curve of the inhibitory effect of the synthetic peptide brap on the bradykinin B2 receptor.

FIG. 6A is the score of allergic rhinitis, and B is the change of score before and after treatment.

FIG. 7A is the standard curve of OD value-EB concentration, and FIG. 7B is the EB content of lung tissue.

FIG. 9A is the dose-response curve of the bradykinin B1 receptor antagonist R892, and FIG. 9B is the dose-response curve of the inhibitory effect of the synthetic peptide brap on the bradykinin B1 receptor.

FIG. 12A is that LPS promotes the release of inflammatory factor IL-6; FIG. 12B shows an influence of the synthetic peptide brap on the release of the inflammatory factor IL-6 induced by LPS (5 mg/kg i.p.) for 6 h; FIG. 12C shows an influence of the synthetic peptide brap on the release of the inflammatory factor IL-6 induced by LPS for 12 h.

FIG. 13A shows that LPS promotes a remarkable increase of inflammatory factor TNF-α content; FIG. 13B is the effect of the synthetic peptide brap on the release of an inflammatory factor TNF-α induced by LPS for 6 h; FIG. 13C is the effect of the synthetic peptide brap on the release of inflammatory factor TNF-α induced by LPS for 12 h.

FIG. 16A is the normal control group; FIG. 16B is the LPS model group; FIG. 16C is the sp2 group; FIG. 16D is the brap intravenous administration high-dose group; FIG. 16E is the brap intravenous administration-middle-dose group; FIG. 16F is the brap intravenous administration low-dose group; FIG. 16G is the brap intranasal administration group; and FIG. 16H is dexamethasone model group (a positive control group).

DETAILED DESCRIPTION OF THE INVENTION

The non-limiting examples below can render a person skilled in the art to understand the present invention more comprehensively, but cannot be used to limit the present invention in any way.

Example 1 Test on the Amino Acid Composition of the Synthetic Peptide Brap 10 mg sample was accurately weighed and put in a hydrolysis tube, and 20 ml of 6 mol/L hydrochloric acid was added, which was treated in vacuum for degasification, then nitrogen was loaded and the tube was sealed. Hydrolysis was performed for 22-24 h at 110° C., and after cooling, the solution was adjusted to a constant volume by deionized water, and mixed evenly. 1 mL hydrolysate was taken accurately and dried in vacuum, and 1 mL deionized water was added for drying by distillation, then 1 mL deionized water was then added for drying by distillation, and 1 mL 0.02 mol/L hydrochloric acid was added accurately for redissolving. The obtained product was filtered by a 0.22 µm filter membrane and tested on an analyzer (HITACHI L-8900 amino acid analyzer).

Figure 1A:
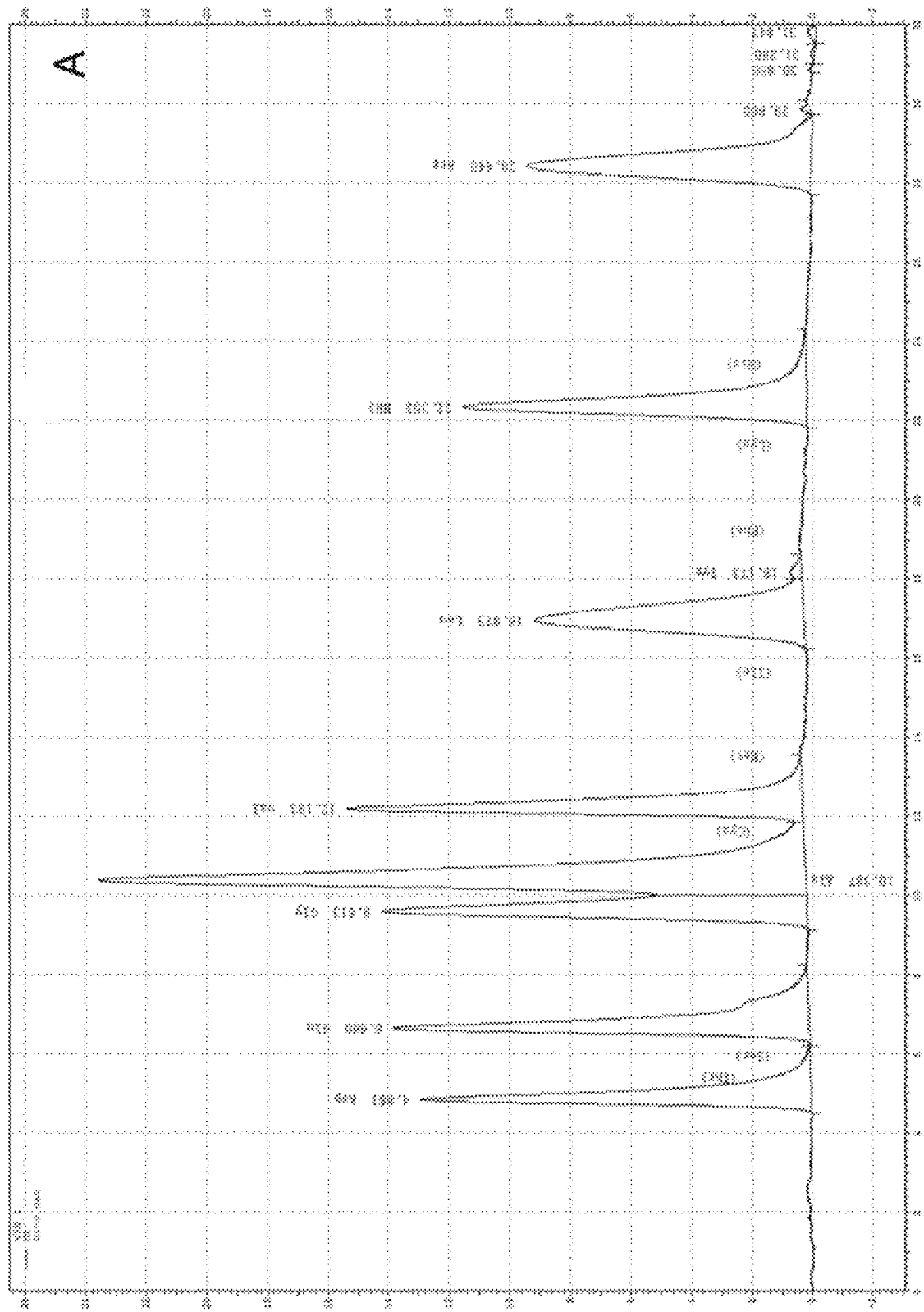
FIGS. 1A-1B show analysis on the amino acid composition of a synthetic peptide brap.
Figure 1B:
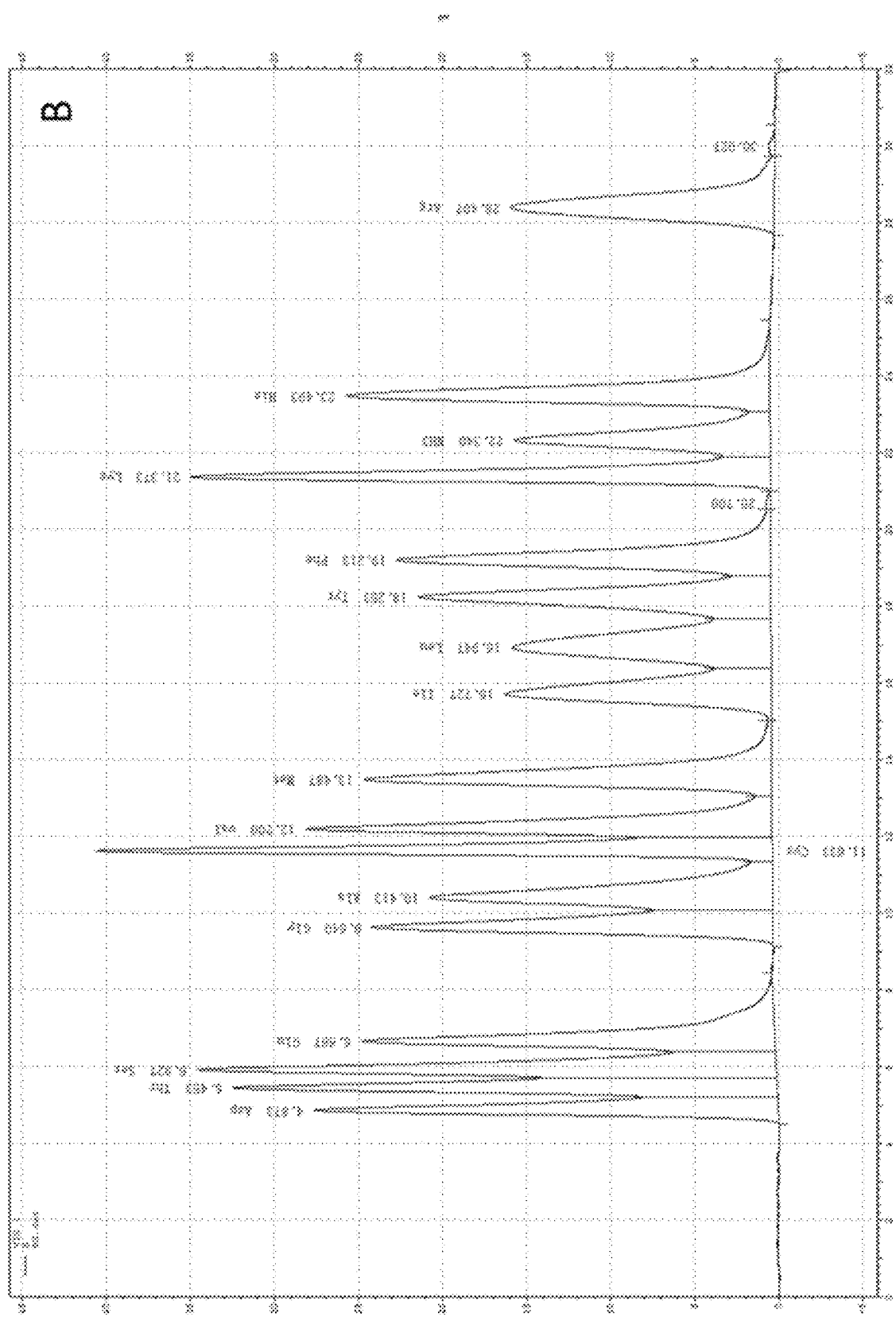

The test results are showed in Table 1 and FIGS. 1a and 1b.

TABLE 1

The amino acid composition and content of the synthetic peptide brap

| Sample | Test item | Test result | unit | Test method |
| --- | --- | --- | --- | --- |
| Synthetic peptide brap | ASP (aspartic acid) | 8.58 | g/100 g | amino acid analyzer |
| | THR (threonine) | not detected | g/100 g | amino acid analyzer |
| | SER (serine) | not detected | g/100 g | amino acid analyzer |
| | GLU (glutamic acid) | 9.39 | g/100 g | amino acid analyzer |
| | GLY (glycine) | 5.10 | g/100 g | amino acid analyzer |
| | ALA (alanine) | 12.09 | g/100 g | amino acid analyzer |
| | CYS (cystine) | not detected | g/100 g | amino acid analyzer |
| | VAL (valine) | 7.30 | g/100 g | amino acid analyzer |
| | MET (methionine) | not detected | g/100 g | amino acid analyzer |
| | ILE (isoleucine) | not detected | g/100 g | amino acid analyzer |
| | LEU (leucine) | 8.69 | g/100 g | amino acid analyzer |
| | TYR (tyrosine) | not detected | g/100 g | amino acid analyzer |
| | PHE (phenylalanine) | not detected | g/100 g | amino acid analyzer |
| | LYS (lysine) | not detected | g/100 g | amino acid analyzer |
| | HIS (histidine) | not detected | g/100 g | amino acid analyzer |
| | ARG (arginine) | 12.25 | g/100 g | amino acid analyzer |
| | PRO (proline) | 18.36 | g/100 g | amino acid analyzer |

It can be seen from Table 1 and FIG. 1 that the synthetic peptide brap is-composed of 8 amino acids.

Figure 2:
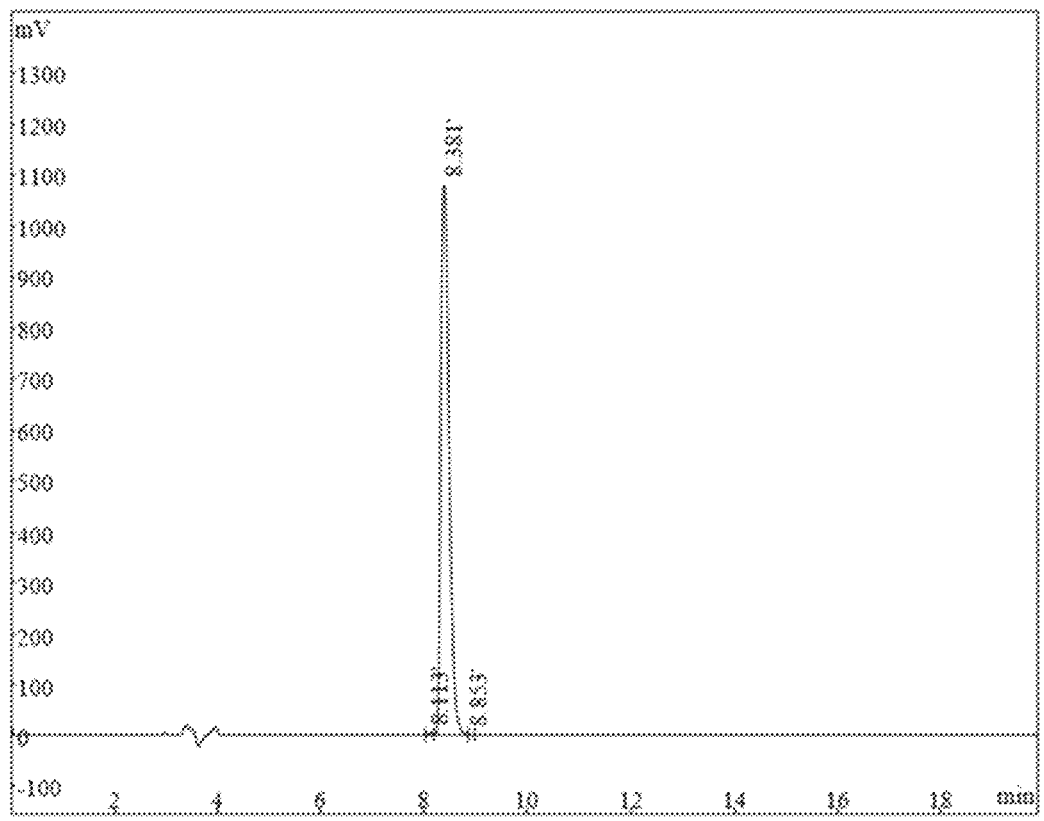
FIG. 2 shows a HPLC result of the synthetic peptide brap.
Figure 3:
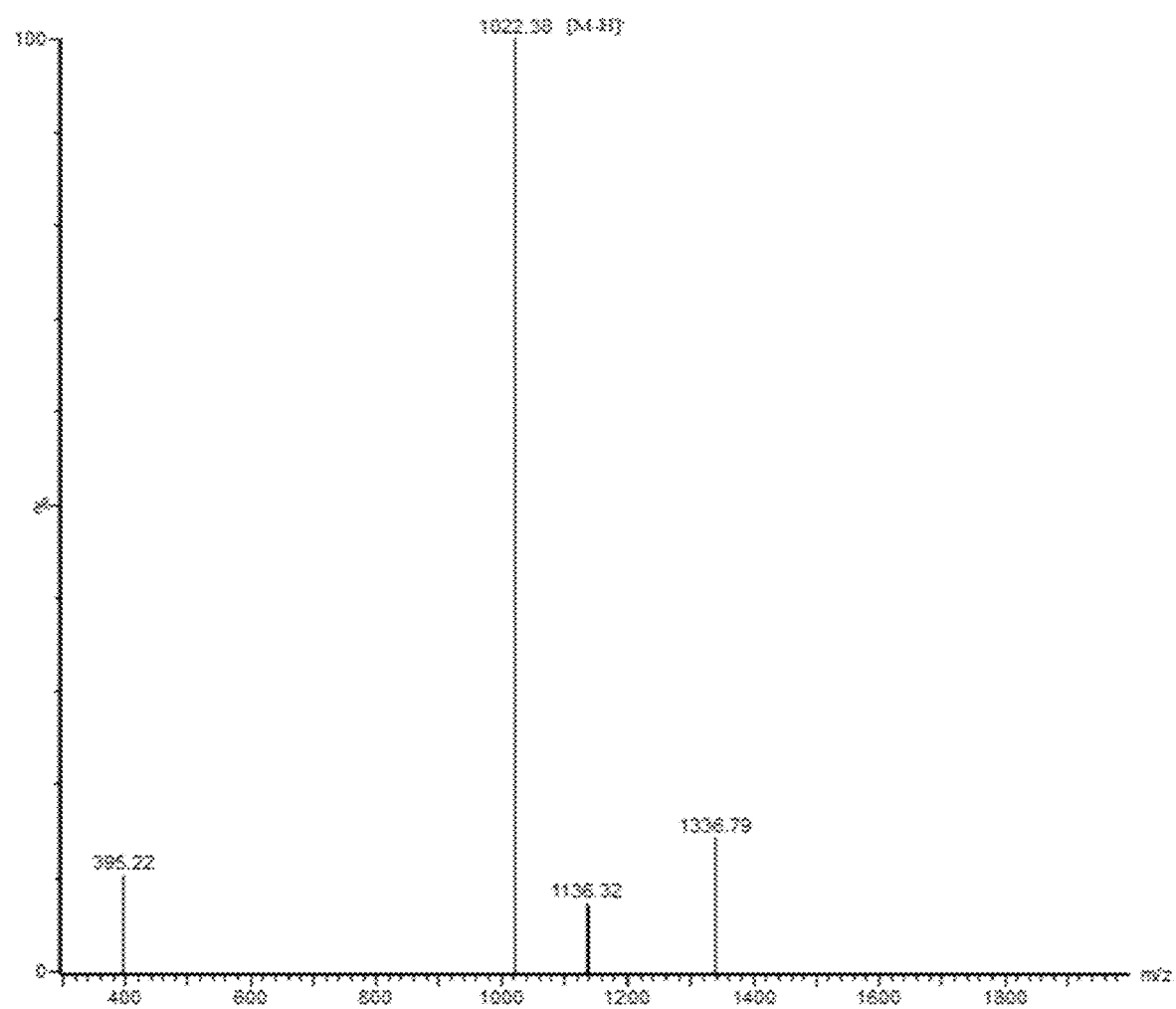
FIG. 3 shows an MS result of the synthetic peptide brap.

Example 2 Synthetic Process, HPLC Purification and Mass Spectrum Identification of the Synthetic Peptide Brap The technique was provided by China Peptides Co., Ltd.
Synthetic procedure: from C-terminal to N-terminal of the sequence, steps were as follows:

a. n equivalents of resin (solid-phase synthesis carrier) was weighed and put in a reactor, and DCM (dichloromethane) was added for swelling for half an hour, then DCM was removed; 2n equivalent first amino acid in the sequence was added, and 2n equivalent DIEA, a proper amount of DMF and DCM (a proper amount refers to bubbling the resin fully); DIEA (diisopropylethylamine), DMF (dimethylformamide), DCM and $N_2$ were added for bubbling reaction for 60 min; then, about 5n equivalent methyl alcohol was added for reacting for half an hour, and reaction liquid was removed; and the obtained product was cleaned by DMF and MEOH;

b. a second amino acid in the sequence (namely, 2n equivalent), 2n equivalent HBTU (1-hydroxy, benzo, trichloroazole tetramethyl hexafluorophosphate), DIEA, and $N_2$ were added for bubbling reaction for half an hour; then liquid was washed out, and ninhydrin was used to test, then end-capping was performed by pyridine and acetic anhydride; finally, the obtained product was cleaned, a proper amount of de-capping solution was added to remove a Fmoc (9-fluorenylmethoxycarbonyl) protecting group, and the obtained product was cleaned and detected by ninhydrin;

c. different amino acids in the sequence were successively added according to the way of step b;

d. a resin was blown-dried by N2 and taken from a reaction column, then poured into a flask, then a certain amount of (a ratio of the cutting fluid to the resin was about 10 ml/g) cutting fluid (composed of 95% TFA, 2% dithioglycol, 2% triisopropylsilane and 1% water) was added to the flask, and vibrated to filter out the resin;

e. a filtrate was obtained, and then a large amount of ether were added to the filtrate to precipitate the crude product, then to centrifuge and wash to obtain the crude product of the sequence shown in SEQ ID No: 1;

The obtained crude product was purified by HPLC, the peptide was lyophilized and detected; and then product identification was performed by mass spectrum. HPLC was shown in FIG. 2; the synthetic peptide brap has a purity of 99.72%; mass spectrum was shown in FIG. 3; the synthetic peptide brap has a theoretical molecular weight of 1023.17; that is, the molecular weight was correct by mass spectrum identification.

Figure 4:
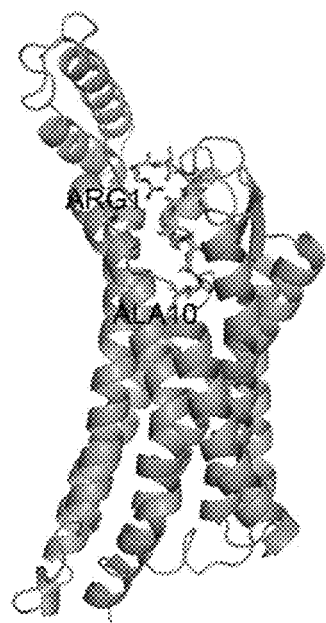
FIG. 4 shows a target-docking test of the synthetic peptide brap to a G-protein-coupled bradykinin B2 receptor.

Example 3 Docking and Binding Modes of a Bradykinin B2 Receptor (B2R) Target to Brap The technique was provided by Nanjing OGPharmaceutical.CO., Ltd.
NCBI Blast was used for PDB library-based sequence alignment to a B2 receptor (B2R) of Bradykinin (BK); 5UNF having a good sequence similarity and percentage of coverage was selected as a template. A homologous modeling block Prime of Schrodinger software package was used for 3D structure modeling of B2R. Based on the modeling parameters, different files capable of obtaining two B2R structures were set; and to ensure the rationality and repeatability of the subsequent docking, they were a knowledge-based receptor structure and an energy-based receptor structure. Further, MDockPeP was used to dock the synthetic peptide brap onto the two receptor structures; and two docking tests were performed in total. In the docking test, the binding positions of the synthetic peptide brap were distributed in the middle of an open pocket composed of transmembrane helixes of a receptor protein (FIG. 4).

Example 4 Detection of an Inhibiting Effect of the Brap to Bradykinin B2 Receptor by an Intracellular Calcium Ion Fluorescent Technique The technique was provided by Wuhan Heyan Biotech Co., Ltd.
HEK293/G15/Bradykinin2 (B2R) Experimental Method: Detection of an Inhibiting Effect of the Synthetic Peptide Brap to Bradykinin B2 Receptor by an Intracellular Calcium Ion Fluorescence Technique Step 1. the HEK293/G15/Bradykinin2 cells whose growth confluence reached 80% were digested with trypsin and counted; the cell were plated at density of $2 \times 10^4$/mL per well on a transparent black-edging 384-well cell culture plate coated with matrigel in advance;

Step 2. the paved 384-well cell culture plate was put in a 5% $CO_2$ 37° C. incubator for overnight culture;

Step 3. the compound synthetic peptide brap was dissolved by HBSS into a 30 mM stock solution on the day of the experiment;

Step 4. 10 μL 4 X no-wash Fluo8 dye was added per well for incubation for 1 h at room temperature;

Step 5. during cell incubation, the compound to be detected was diluted 5 folds by HBSS containing 0.1% BSA; a positive inhibitor has an initial concentration of 10 μM.

Step 6. EC10, EC20 and EC80 represented different stimulus intensity to the B2 receptor;

Step 7. the prepared compound to be detected was added to a cell culture plate, and put in FLIPR for data recording.

Figure 5A:
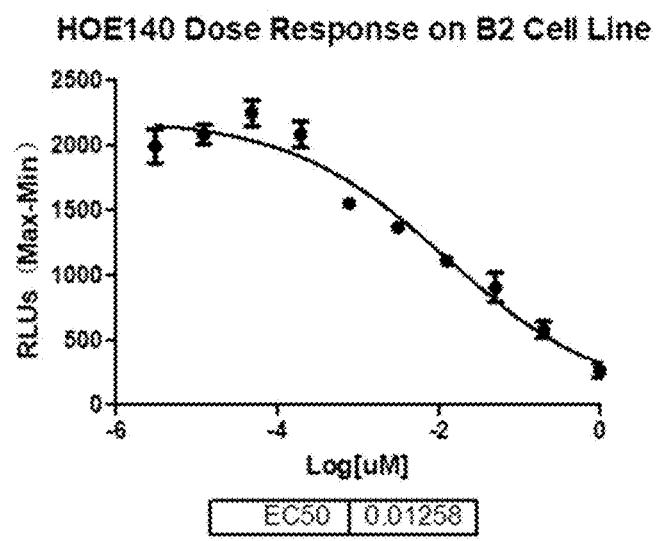
FIGS. 5A-5B show the inhibitory effect of the synthetic peptide brap on the bradykinin B2 receptor.
Figure 5B:
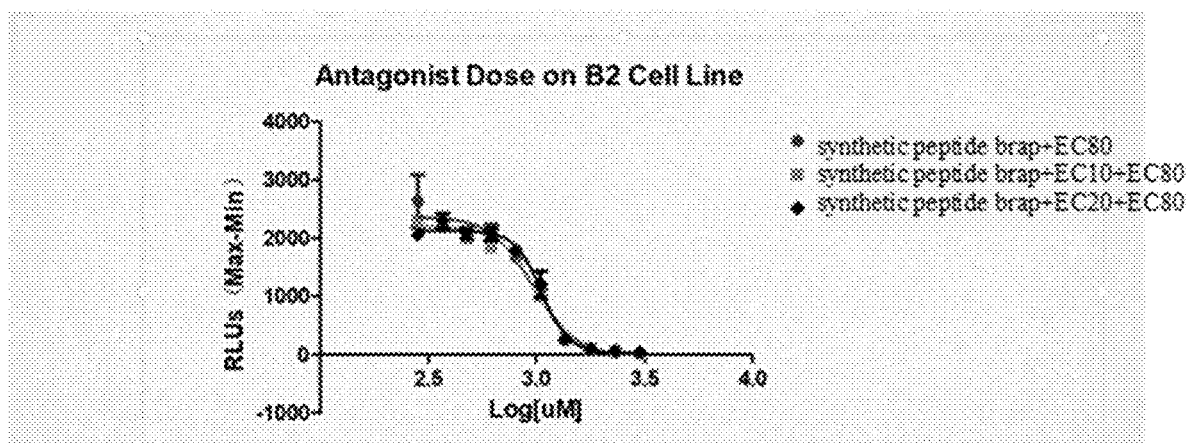

As shown in FIGS. 5a and 5b, results show that the test curve is smooth and is a distinct s-curve; and IC50 is at 1 mM around.

Example 5 Test on Pharmacodynamic Effect of the Synthetic Peptide Brap on Rat Allergic Nasal Inflammation by Intranasal Administration The technique was provided by Shanghai Meixuan Biological Science and Technology Co., Ltd.
I. Preparation of an Animal Model
1. Modeling Method:
SD rat modeling: two stages of intraperitoneal injection for sensitization and intranasal dripping for stimulation. Ovalbumin was injected intraperitoneally, and 1 mg ovalbumin (V-class Sigma, USA) was dissolved in 1 ml normal saline, and 30 mg of aluminum hydroxide was added as an immunologic adjuvant. Each rat was intraperitoneally injected 1 ml ovalbumin suspension prepared above with 1 ml/time every other day and for 7 times in total; and stimulated intranasally with ovalbumin on the 15th day; 20 mg ovalbumin (V-class Sigma, USA) were dissolved in 1 ml normal saline to be prepared into a 2% solution; and the 2% ovalbumin solution was used for stimulation by nasal dripping; and 50 ul nasal drips were administered in each of the nasal cavities of each rat for 7 consecutive days.

Blank control group: 30 mg of aluminum hydroxide+1 ml of normal saline were mixed evenly, and then injected intraperitoneally; and the method was the same as the above.

Normal saline was dripped into nasal cavities on the 15th day.

2. Symptom Assessment

After the final nasal dripping was performed, each rat was observed and evaluated according to a scoring table: Sneezing, nose scratching, gasping and nasal secretions II. Animal Model Treatment and Evaluation 1. Administration way: a drug was administered with a micro-sampling gun, bilateral nasal cavities of a rat were administered with 50 μL/side, after being administered for 20 min, a 2% ovalbumin solution was administered to bilateral nasal cavities of the rat; 50 μL/side nasal dripping was administered for provocation; the above treatment was performed for 4 consecutive weeks to observe the pharmacodynamic effect.

2. Medicament Preparation

High-dose synthetic peptide brap: a synthetic peptide brap freeze-dried powder (5 mg/bottle) was taken, and 1.63 ml sterile saline solution was added for dissolving;

medium-dose synthetic peptide brap: a synthetic peptide brap freeze-dried powder (5 mg/bottle) was taken, and 4.89 ml sterile saline solution was added for dissolving;

low-dose synthetic peptide brap: a synthetic peptide brap freeze-dried powder (5 mg/bottle) was taken, and 14.67 ml sterile saline solution was added for dissolving;

meanwhile, high-dose synthetic peptide sp2 group and medium-dose synthetic peptide sp2 group were configured as control groups; the high-dose synthetic peptide sp2 group had a concentration the same as that of the high-dose synthetic peptide brap group; and the medium-dose synthetic peptide sp2 group had a concentration the same as that of the medium-dose synthetic peptide brap group. The synthetic peptide sp2 had an amino acid sequence as shown in SEQ ID No: 2.

3. Symptom Assessment

Figure 6A:
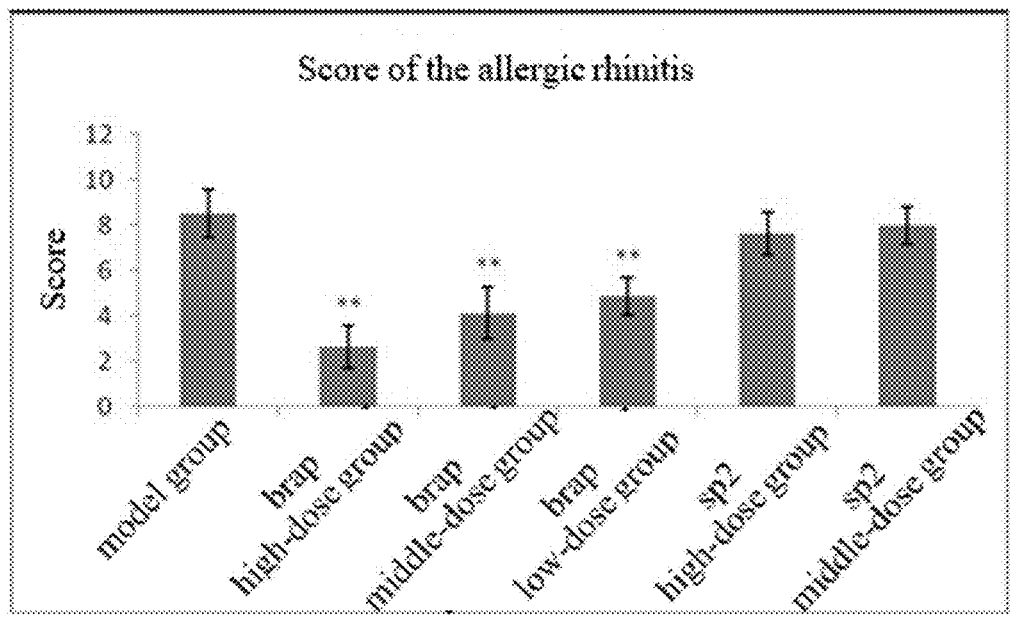
FIGS. 6A and 6B show pharmacodynamic effect of the synthetic peptide brap in rate allergic nasal inflammation by intranasal administration.
Figure 6B:
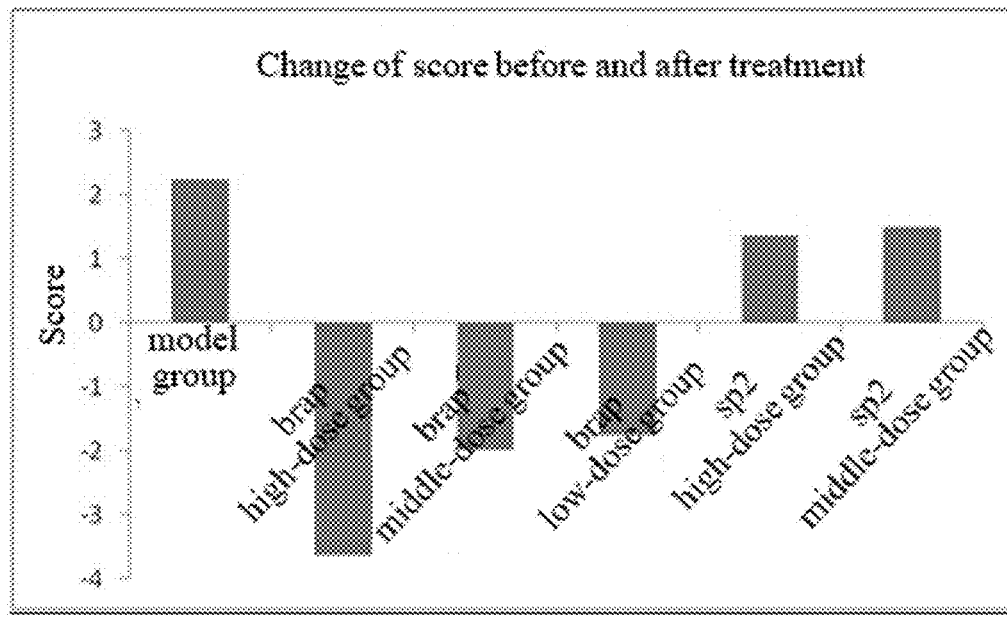

After being challenged by the final OVA, the rat was scored. Experimental results were as shown in FIGS. 6A and 6B; FIG. 6A shows pharmacodynamic effect scoring of the synthetic peptide brap on allergic rhinitis rats; and the experiment results show that compared with the model group, the high, medium and low-dose synthetic peptide brap can improve the OVA-induced allergic rhinitis symptoms; moreover, the scoring has significance of difference, which hints that the synthetic peptide brap has a good therapeutic effect on allergic rhinitis. FIG. 6B shows scoring changes on rats before and after treatment; rats in the model group were continuously stimulated by OVA, the scoring rises sharply; and the rat mortality increases continually (the mortality is 2/54=3.7% during modeling, and the mortality is 2/8=25% in the therapeutic period of the later administration); after receiving the treatment of the medium-dose group and high-dose group of the synthetic peptide sp2, the scoring thereof increases as well, which hints that the synthetic peptide sp2 cannot completely counteract the negative effects from the OVA simulation; after receiving the treatment of the high, medium, and low-dose group of the synthetic peptide brap, the scoring thereof decreases, which hints that the synthetic peptide brap completely counteracts the OVA simulation effect during the period of treatment, and has a certain effect on the recovery of the rat.

Example 6 Influence of Nasal Administration of Synthetic Peptide Brap on BK-Induced Pulmonary Microvascular Leakage in Guinea Pigs The technique was provided by Shanghai Meixuan Biological Science and Technology Co., Ltd.

I. Animal Grouping and Treatment

Male guinea pigs weighing 400 g±5% were randomly divided into 6 groups, 6 per group.

1. normal control group: an equal volume of normal saline was injected intravenously on the lateral foot vein, for 3 days;

2. model group: an equal volume of normal saline was injected intravenously on the lateral foot vein, for 3 days;

3. positive control group: 1.25 mg/3 ml/kg BW dexamethasone was injected intravenously on the lateral foot vein, for 3 days;

4. high-dose synthetic peptide brap group: bilateral nasal cavities of the guinea pig were injected the synthetic peptide brap having a concentration of 3.0 mM/L by a micro-sampling gun with 50 μL/side/day for 3 days;

5. medium-dose synthetic peptide brap group: bilateral nasal cavities of the guinea pig were injected the synthetic peptide brap having a concentration of 1.0 mM/L by a micro-sampling gun with 50 μL/side/day for 3 days;

6. low-dose synthetic peptide brap group: bilateral nasal cavities of the guinea pig were injected the synthetic peptide brap having a concentration of 0.33 mM/L by a micro-sampling gun with 50 μL/side/day for 3 days.

II. Detection of Guinea Pig Pulmonary Leak

1. The guinea pig was administered for 3 days, and 20 min after the last administration, 1% EB (20 mg/kg) and 15 nmoL/kg bradykinin (diluted to 10 nmoL/mL by normal saline, namely, 15 nmoL/kg based on 1.5 mL/kg weight) were successively injected intravenously on the lateral side of foot; and the guinea pig in the normal group were not injected with EB and bradykinin.

Figure 7A:
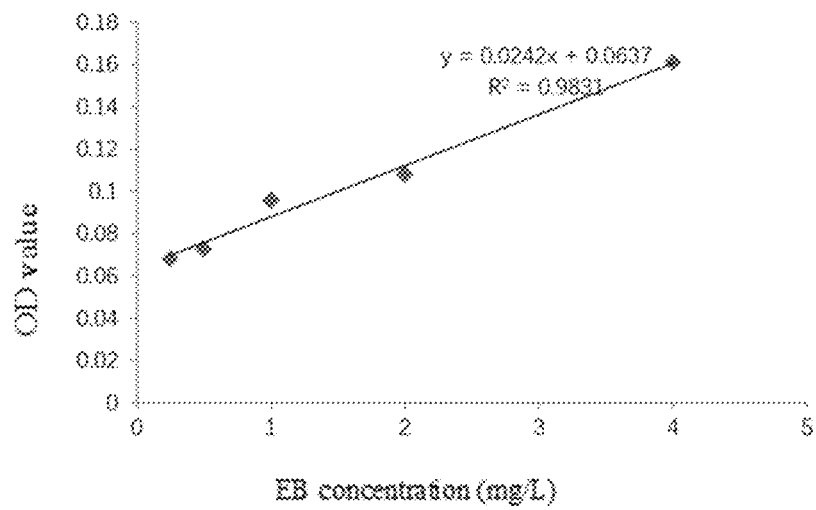
FIGS. 7A-7B show significant inhibition of the synthetic peptide brap on BK-induced pulmonary microvascular leakage in guinea pigs through intranasal administration.
Figure 7B:
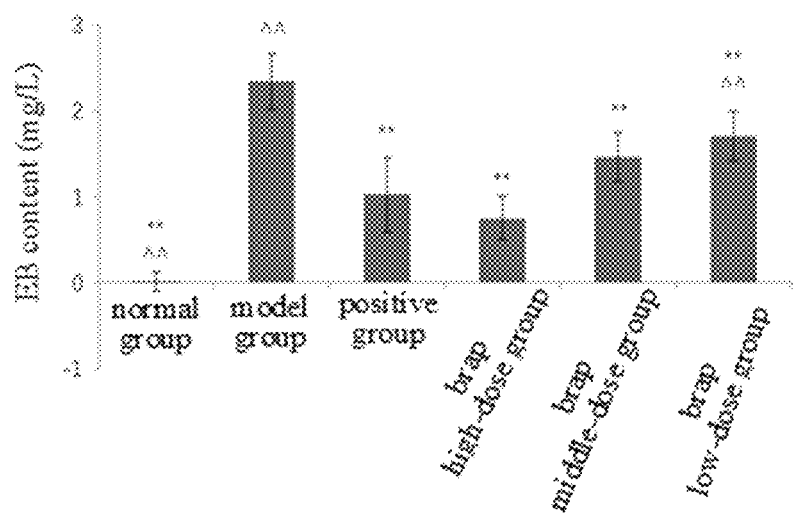
Figure 8:
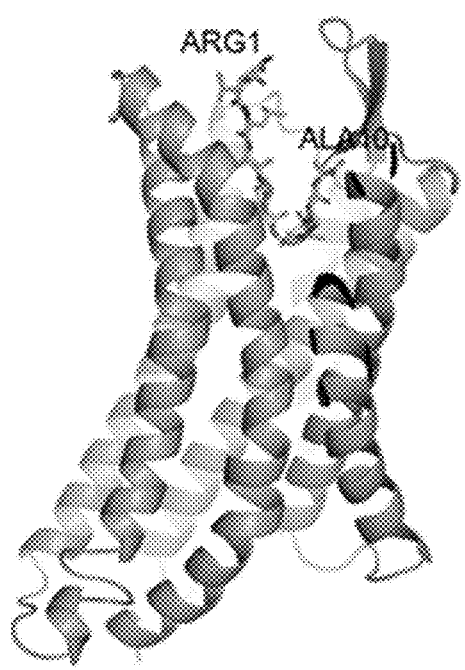
FIG. 8 shows the target docking of the synthetic peptide brap to the G-protein-coupled bradykinin B1 receptor.

2. Measurement of EB in lung tissue: after bradykinin was injected for 30 min, an animal was narcotized and killed by taking blood on the carotid artery for blood routine examination; thoracic cavity was opened to cut ventriculus dexter and left atrium; pulmonary artery intubation was performed; 30 mL normal saline was used for guinea pig pulmonary circulation till effluent was clear. Inferior lobe of right lung was taken out, and blood on the surface thereof was washed by normal saline to suck water dry by a filter paper; 100 mg were taken and cut into pieces; placed in a 2 mL formamide solution for incubation in a water bath for 24 h at 45° C. The solution was centrifuged for 5 min at 1500 rpm/min; supernatant was taken to measure the absorbance with a wavelength of 620 nm. The content of EB in lung tissues was obtained by an EB standard curve (as shown in FIG. 7A), as shown in FIG. 7B.

3. Preparation of an EB standard curve: 0.1 mL 0.1% EB solution was taken accurately and added 0.9 mL normal saline to be prepared into 1 mL 0.01% EB standard solution; 0.1 mL EB standard solution was taken and added formamide to 2 mL with a final concentration of 5 mg/L; then the solution was diluted by formamide to 4, 2, 1, and 0.5 mg/L. An absorbancy OD value was measured at a wavelength of 620 nm; OD value was denoted y-coordinate; EB concentration was denoted by x-coordinate; then a standard curve of OD value-EB concentration was drawn, as shown in FIG. 7A.

III. Experimental Analysis

1. Evans blue (EB) may be combined with albumin; EB exudation reflects the exudation condition of a protein; the content of EB leaking from lung tissues is measured to reflect the degree of the pulmonary microvascular permeability and the degree of pulmonary microvascular leakage. Compared with the normal control group, the content of EB in lung tissues of the model group increases significantly (** indicates P<0.01); the content of EB in lung tissues of the low, medium, and high-dose groups of the synthetic peptide brap is obviously lower than that in the model group (P<0.01); and there is a dose-response relationship. Compared with the positive control group, there is no significant difference (^^indicates P>0.05) except for the low-dose group.

2. Compared with the normal control group, the content of EB in lung tissues of the model group increases significantly (** indicates P<0.001); the content of EB in lung tissues of the low-, medium-, and high-dose groups of the synthetic peptide brap is obviously lower than that in the model group (P<0.01); there is a dose-response relationship. Compared with the positive control group, there is no significant difference (^^ indicates P>0.05).

Example 7 Docking and Binding Modes of a Bradykinin B1 Receptor Target to the Brap The technique was provided by Nanjing OGPharmaceutical. Co., Ltd.

1. NCBI Blast was used to select a B1 receptor (B1R) template of Bradykinin (BK); and based on the sequence alignment of PDB library, 5UNF having a good sequence similarity and percentage of coverage was selected as a template.

2. A homologous modeling block Prime of Schrodinger software package was used for 3D structure modeling of B1.

Based on the modeling parameters, different files capable of obtaining two B2R structures were set; they were a knowledge-based receptor structure and an energy-based receptor structure.

3. MDockPeP was used to dock the synthetic peptide brap onto the two receptor structures; and two docking tests were performed in total.

4. The optimal binding mode in the docking test was subjected to interactive brap-receptor energy decomposition, which reveals the energy contribution of amino acid residues in the synthetic peptide brap and the binding mode to the B1 receptor.

① Homology modeling of a B1 receptor structure of Bradykinin (BK)

The sequence of the B1 receptor was downloaded from a uniprot library to obtain the sequence of the B1 receptor in homologous modeling, as shown in SEQ ID No: 7.

② Molecular docking of a Bradykinin (BK) B1 receptor to the synthetic peptide brap:

MDockPeP was used for the docking of a B1 receptor protein with a structure of brap.

brap is a 10-peptide compound composed of 8 kinds of amino acids.

In the diagram, green denotes receptor protein molecules, and blue denotes molecules of the synthetic peptide brap.

③ Energy contribution of each residue on the synthetic peptide brap was calculated in Model to further study interacting residues between B1 (a receptor) and brap (a ligand); for each residue on brap, the receptor residue within a range of distance less than 4 Å was defined as a contact residue. Based on this, energy contribution of each residue on brap was calculated.

In the diagram, green denotes receptor protein molecules, and light blue denotes brap molecules.

The synthetic peptide brap is bonded into a receptor pocket in U-shaped.

Example 8 Inhibitory Effect of the Synthetic Peptide Brap on a Bradykinin B1 Receptor The technique was provided by Wuhan Heyan Biotech Co., Ltd.

1. Experimental method of HEK293/G15/Bradykinin1:

Cell Resuscitation:

HEK293/Gα15/B cells to be resuscitated were rapidly taken from a liquid nitrogen container and thawed in a water bath at 37° C. A cell suspension was rapidly added to a preheated DMEM+10% FBS culture medium, and the medium was put to a centrifugal machine for centrifugation for 5 min at 1000 rpm. A centrifugal tube was removed, and supernate was discarded; a fresh preheated culture medium was added to the centrifugal tube to resuspend cells, and a cell suspension was added to a petri dish for culture at 37° C. under the condition of 5% $CO_2$.

Cell passage HEK293/Gα15/B1 cells stably expressing the B1 receptor were cultured in DMEM+10% FBS; cell culture conditions: routine culture of HEK293/Gα15/B1 cell line, cells were subcultured on a medium containing 10% fetal calf serum and DMEM.

The cells were digested by 0.25% trypsin when grew 80-90% of the petri dish; and cells were resuspended by a new culture medium and subcultured in a proper proportion for once about 2-3 d.

Experimental Procedure

1. HEK293/G15/Bradykinin1 cells whose growth confluence up to 80% were digested by trypsin and counted; then paved onto a transparent black-edging 384-well cell culture plate coated by matrigel in advance according to a density of $2 \times 10^4$/mL per well.

2. The paved 384-well cell culture plate was put in a 5% $CO_2$ 37° C. incubator for culturing, staying over the night.

3. On the day of the experiment, the compound synthetic peptide brap was dissolved into a 30 mM stock solution with HBSS.

4. 10 μL 4 X no-wash Fluo8 dye was added per 384-well plate for incubation for 1 h at room temperature.

5. During cell incubation, the compound to be detected was diluted 5 folds by HBSS containing 0.1% BSA. A positive inhibitor has an initial concentration of 10 μM.

6. EC10 had a final stimulation concentration of 0.3 nM; EC20 had a final stimulation concentration of 0.6 nM; and EC80 irritant had a final concentration of 18 nM.

7. The prepared compound was added to a cell culture plate for data recording in FLIPR.

Figure 9A:
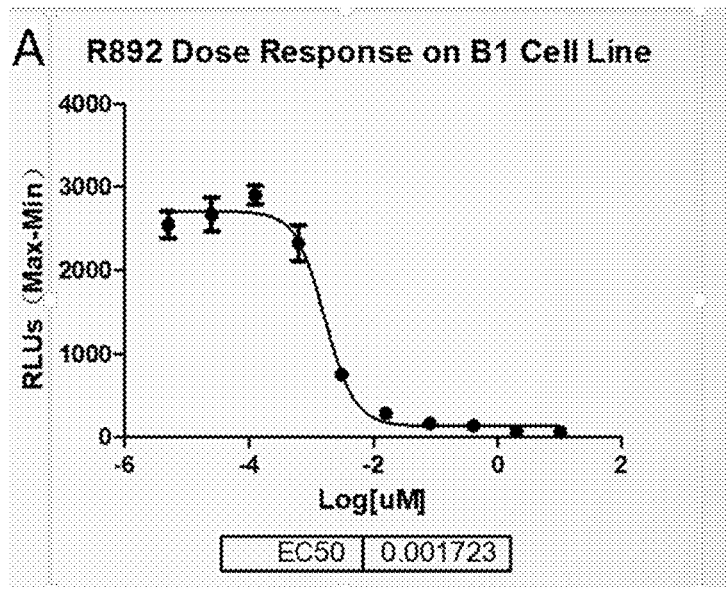
FIGS. 9A-9B show the inhibitory effect of the synthetic peptide brap on the bradykinin B1 receptor.
Figure 9B:
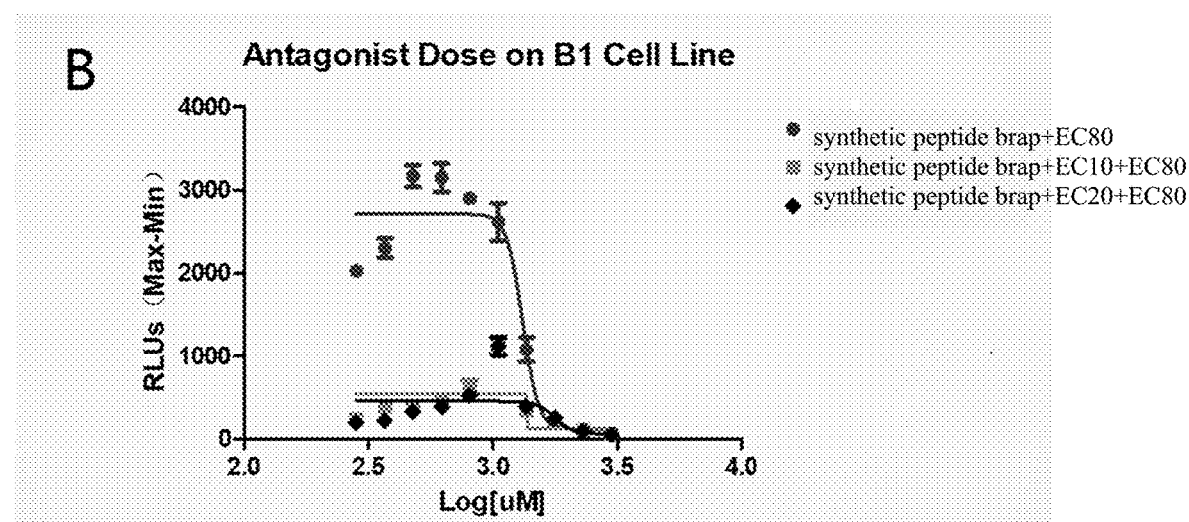

Experimental results were as shown in FIGS. 9A and 9B. A Bradykinin mixed solution (brap+Vehicle, brap+EC10 and brap+EC20) was added to a cell line, and then continuously incubated for 15 min, then an EC80 irritant was added to test the inhibitory activity of the compound.

The results show that brap and EC80 work together, and there is an obvious S-shaped curve, indicating that the excessive activation of the B1 receptor is obviously inhibited; the compound both acting together with EC10 and EC20 has no obvious effect; it is speculated that the previous reaction has released too many calcium ions, which cannot cause a secondary signal within a short period of time.

Example 9 Protective Effect of the Synthetic Peptide Brap on LPS-Induced Acute Lung Injury in Mice The technique was provided by Shanghai Meixuan Biological Science and Technology Co., Ltd.

I. Animal Grouping and Treatment

1. Grade-SPF male Balb/C mice, body weight: 20±2 g, and n=48
2. Feeding conditions: mice were fed in SPF aseptic conditions, alternatively illuminated for 12 h and supplied adequate food and water in a constant-temperature environment at 25° C.
3. Grouping and treatment: mice were randomly divided into 8 groups (A-H), 6 pcs./group;
3-1: 3 different treatments were given for 3 consecutive days respectively before modeling:
A. normal control group: normal saline was injected via the tail vein for once/day;
B. LPS model group: normal saline was injected via the tail vein for once/day;
C. model sp2 administration group: sp2 (16 mg/kgBW) was injected via the tail vein for once/day;
D. model high-dose brap administration group: brap (16 mg/kgBW) was injected via the tail vein for once/day;
E. model medium-dose brap administration group: brap (8 mg/kgBW) was injected via the tail vein for once/day;
F. model low-dose brap administration group: brap (4 mg/kgBW) was injected via the tail vein for once/day;
G. model brap intranasal administration group: brap (3 mM) was administered nasal administration on both sides, 15 μl/each side; once a day;
H. model dexamethasone administration group (a positive control group): dexamethasone, DEX, 5 mg/kg was injected intraperitoneally for once a day.
3-2. The day of the experiment, that is, the day of modeling:
Animals from groups A-H were continuously administered the above treatments for 30 min respectively, then group A was intraperitoneally injected isopyknic normal saline, and other groups were intraperitoneally injected LPS 5 mg/kgBW.

II. Pathological Examination for HE Dyeing of Lung Tissues

Experimental Steps

1. Tissue section and extending
2. Tissues were dewaxed and hydrated.
3. Tissues were dyed with a hematoxylin stain for 5-20 min (adjusted according to different tissues and experimental requirements), and washed by tap water.
4. Then, tissues were differentiated by a differentiation solution for 30 s.
5. Tissues were soaked by tap water for 15 min or warm water (about 50° C.) for 5 min.
6. Tissues were put in an Eosin stain for 2 min (adjusted according to different tissues and experimental requirements), and washed by tap water.
7. Then, the tissues were soaked by tap water for 5 min.

Figure 16A:
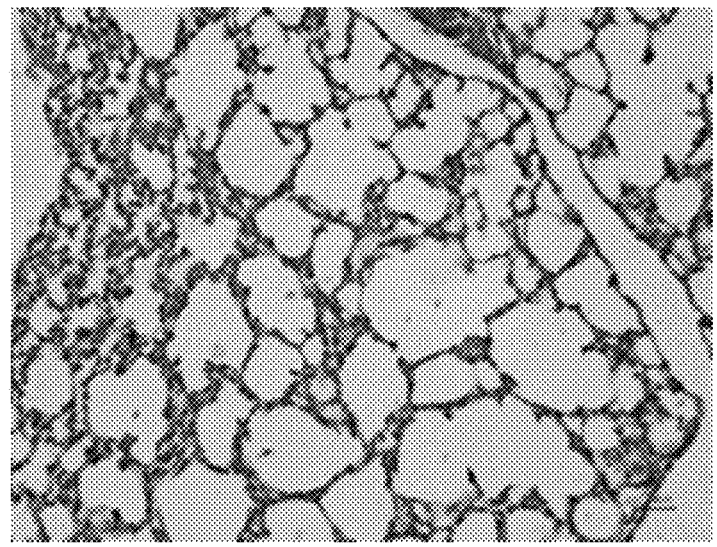
FIGS. 16A-16H show that brap obviously protects lung injury induced by LPS.
Figure 16B:
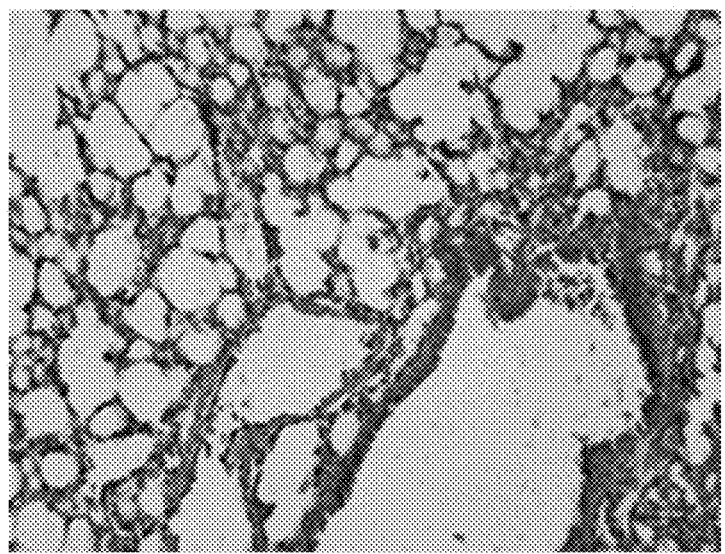
Figure 16C:
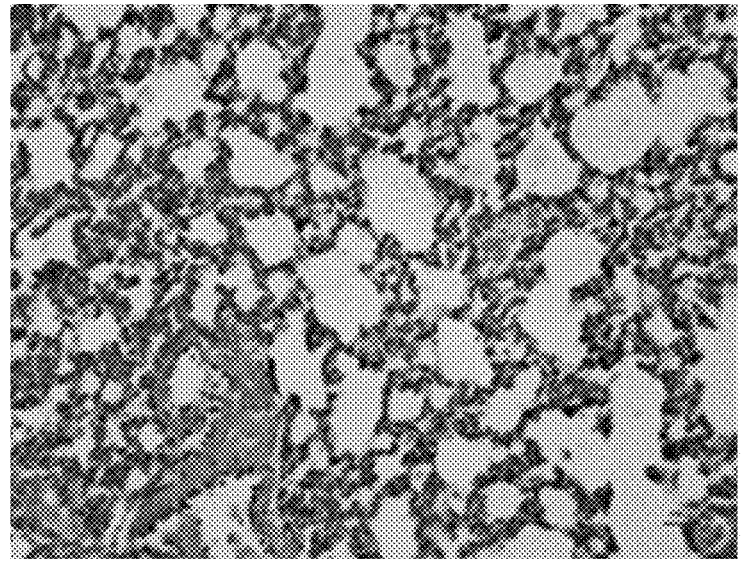
Figure 16D:
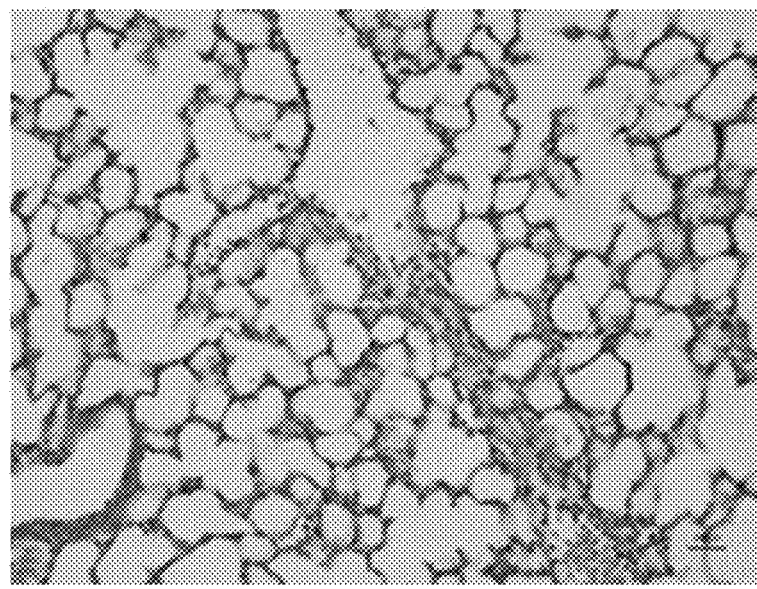
Figure 16E:
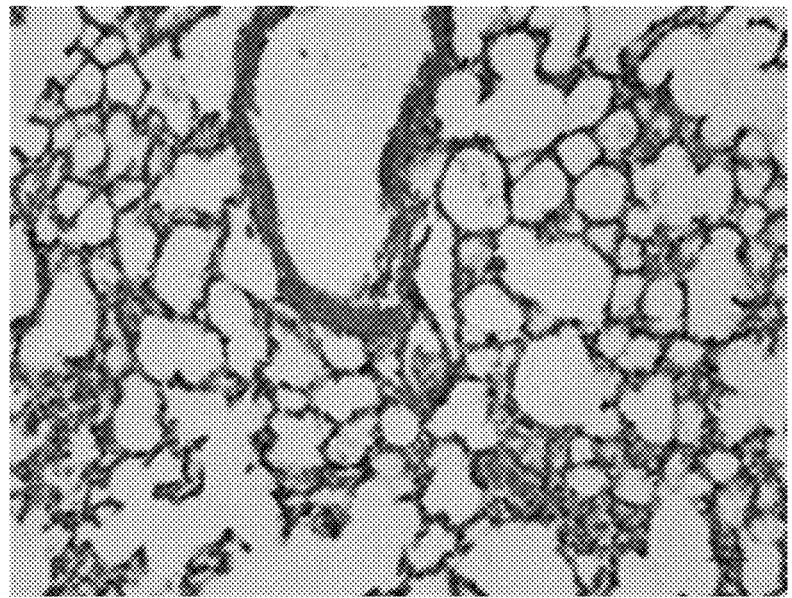
Figure 16F:
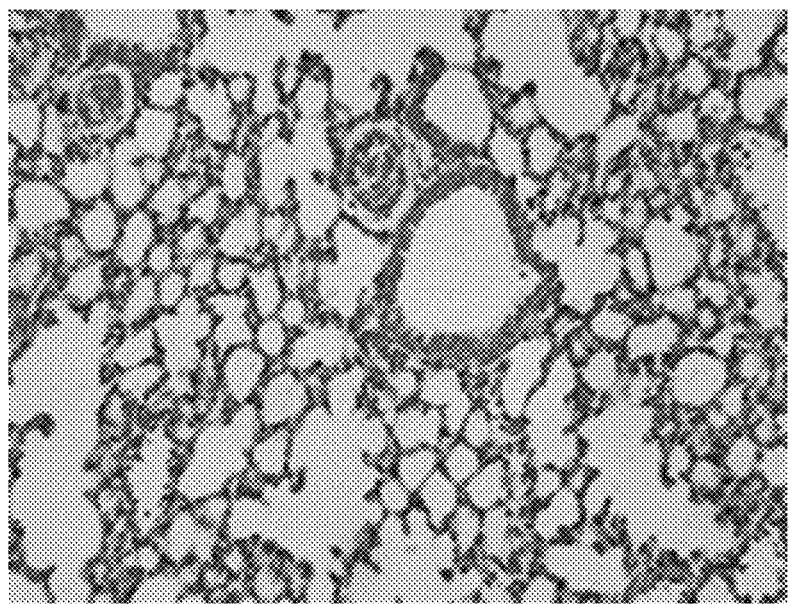
Figure 16G:
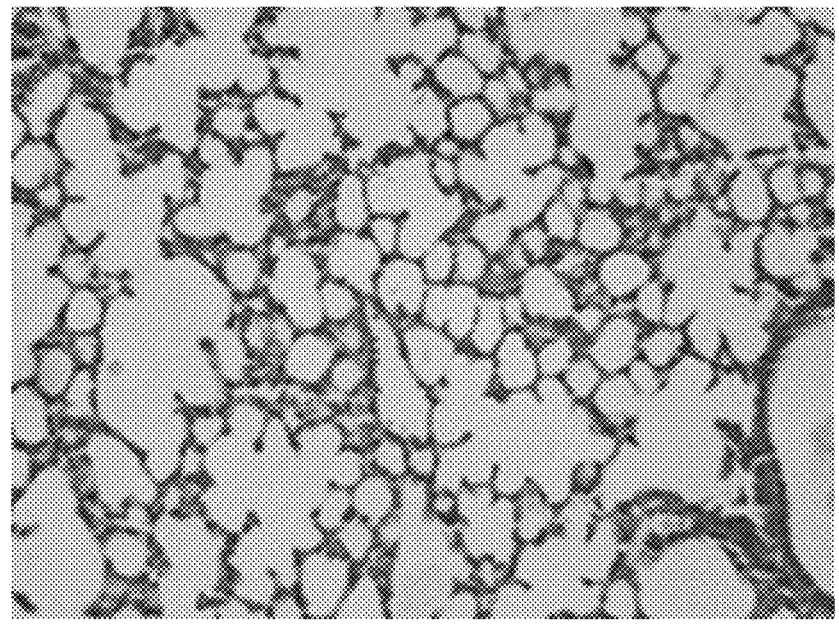
Figure 16H:
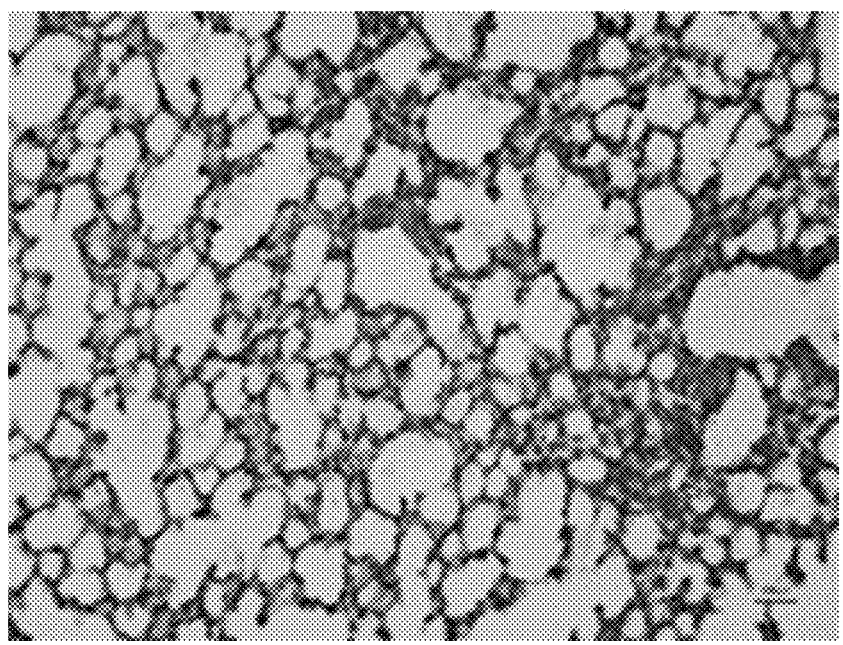

8. Dehydration by gradient alcohol: Tissues were dehydrated by 95%, 100% I, and 100% II for 1 min each;
9. Transparency by xylene: tissues were subjected to xylene I and II for 10 min.
10. Neutral balsam mounting.
11. Then, it was put and dried in an oven at 60° C., and observed under microscope.
Experimental results were as shown in FIGS. 16A-16H.
Result Analysis:
Model group: thickened pulmonary septum, inflammatory cell infiltration, and focal fusion of pulmonary septum were seen. No abnormality can be seen in the high-dose brap intravenous administration group (D) and brap intranasal administration group (G).
FIG. 16B shows a comparison between an LPS model group and a normal control group (FIG. 16A); thickened pulmonary septum, inflammatory cell infiltration, and focal fusion of pulmonary septum were seen. FIG. 16C is an LPS+synthetic peptide sp2 group, and inflammatory cell infiltration is obvious; FIG. 16D is a high-dose LPS+brap group, no thickened pulmonary septum and no obvious inflammatory cell infiltration are found; groups E and F are respectively medium and low-dose groups of LPS+brap; with the decrease of the brap dose, inflammatory cell infiltration begins to appear; group G is an intranasal administration group which is similar to group D, no obvious abnormality is found; group H is a dexamethasone positive control group, inflammatory cell infiltration is more obvious, and no focal fusion of pulmonary septum is found.

Example 10 Detection of Endotoxin Content in a Blood Sample

Detection of Endotoxin Content in a Blood Sample
1. Instrument

| Instrument | Manufacturers | Item No. |
| --- | --- | --- |
| multifunctional microplate reader | Beijing Perlong | DNM-9602 |

2. Reagent

| Reagent | Manufacturers | Item No. |
| --- | --- | --- |
| Endotoxin test LAL kit | Xiamen Bioendo Technology Co., Ltd | EC80545 |

Experimental Steps

The detection was performed according to the specification of the endotoxin test LAL (Limulus Amebocyte Lysate) kit:
(1) anticoagulant venous blood of each group of mice constructed in example 9 was taken and centrifuged for 2 min at 3000 rpm/min; 100 ul supernate was taken and added to a 0.9 ml sample treating fluid;
(2) the above sample was put in a 70° C. dry-heat sterilization box for 10 min, then cooled by running water;
(3) concentration gradient of an endotoxin standard was 1.0, 0.5, 0.25 and 0.1 EU/ml;
(4) several endotoxin-free test tubes were taken, and 100 ul water for detecting bacterial endotoxin, an endotoxin standard and a test product were added respectively;

(6) 100 ul TAL solution was added, mixed evenly, and covered by a silver paper, and incubated for 10 min at 37° C.;

(7) 100 ul developing-matrix solution was added, mixed evenly, and incubated for 6 min at 37° C.;

(8) 500 ul azo reagent 1 was added and mixed evenly;

(9) 500 ul azo reagent 2 was added and mixed evenly;

(10) 500 ul azo reagent 3 was added, mixed evenly, standing for 5 min;

(11) OD value was measured at 545 nm.

Figure 10:
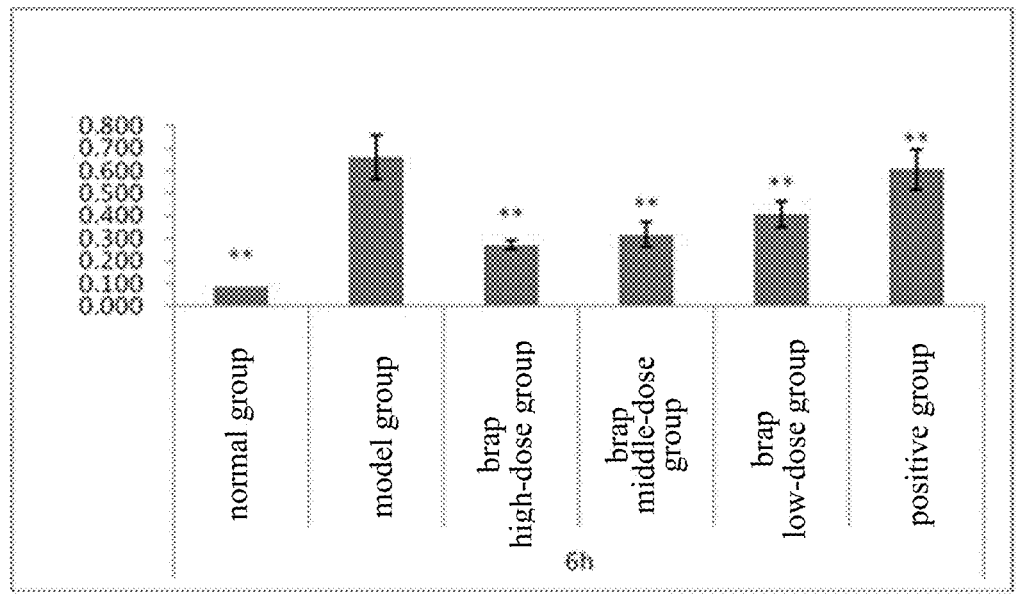
FIG. 10 shows that brap obviously decreases the remarkable increase of LPS-induced endotoxin level in blood.

Experimental results were as shown in FIG. 10. Compared with the normal group, after LPS 5 mg/kg BW were intraperitoneally injected for 6 h, the endotoxin level in mice blood increases significantly; and there was significance of difference; and compared with the model group, the blood endotoxin level in low, medium and high-dose synthetic peptide brap groups was obviously below that in the model group; and there was a dose-response relationship.

Example 11 Detection of IL6 mRNA Expression in Lung Tissues with qPCR

Experimental Steps

Reagent

| Reagent | Manufacturers | Item No. |
|---|---|---|
| RNA Extraction kits (magnetic bead method) | Shanghai Meixuan Biological Science and Technology Ltd | MX0015 |
| RT reagent Kit | Takara | RR047A |
| SYBR Premix Ex Taq | Shanghai Meixuan Biological Science and Technology Ltd | MX200017 |
| Nuclease-free water | Ambion | cat#AM99386 |
| Ethyl alcohol | Sinopharm Chemical Reagent Co., Ltd | AR10009218 (analytically pure) |
| Trichloromethane | Shanghai Chemical Reagent Factory No.1 | Reagent 2006-06-08 |

1. Sample preparation 1.1 Lung tissue sample: a fresh lung tissue sample from each group of mice constructed in example 9 was taken and quick-frozen by liquid nitrogen as quickly as possible, and kept at −8° C.

2. Extraction of total RNA (a total RNA extraction kit via a paramagnetic particle method was used)

2.1 The tissue sample was cut into small pieces, and ground (50 mg) to powder via liquid nitrogen, and transferred to a 1.5 ml tube free of RNA enzyme (cell sample and other liquid samples required no grinding, and were directly put to the next step).

2.2 Total RNA extraction 3. qPCR reaction

Using the operational method of Applied Biosystems 7300/7500/7500 Fast Real-Time PCR System and StepOnePlus™Real-Time PCR System 1. Preparation of a PCR reaction liquid

| Reagent | Use amount |
|---|---|
| SYBR ® Premix Ex Taq | 10.0 μl |
| Enzyme mixture | 2.5 μl |
| PCR Forward Primer (10 μM) | 1 μl |
| PCR Reverse Primer (10 μM) | 1 μl |
| PCR reverse transcription Primer (10 uM) | 0.5 μl |
| RNA template | 2.0 μl |
| dH$_2$O (sterile purified water) | 3.0 μl |
| Total | 20.0 μl |

2. Real Time PCR reaction was performed.

3. Experimental result analysis.

At the end of the reaction, an amplification curve and dissociation curve of Real Time PCR were confirmed, and $2^{-\Delta\Delta ct}$ and the like were calculated.

4. Primer sequence

| Gene | Forward primer | Reverse primer |
|---|---|---|
| IL6 | SEQ ID No: 3: CCACCGGGAACGAAAGAGAA | SEQ ID No: 4: GAGAAGGCAACTGGACCGAA |
| GAPDH | SEQ ID No: 5: GACAGCCGCATCTTCTTGTG | SEQ ID No: 6: AATCCGTTCACACCGACCTT |

Figure 11:
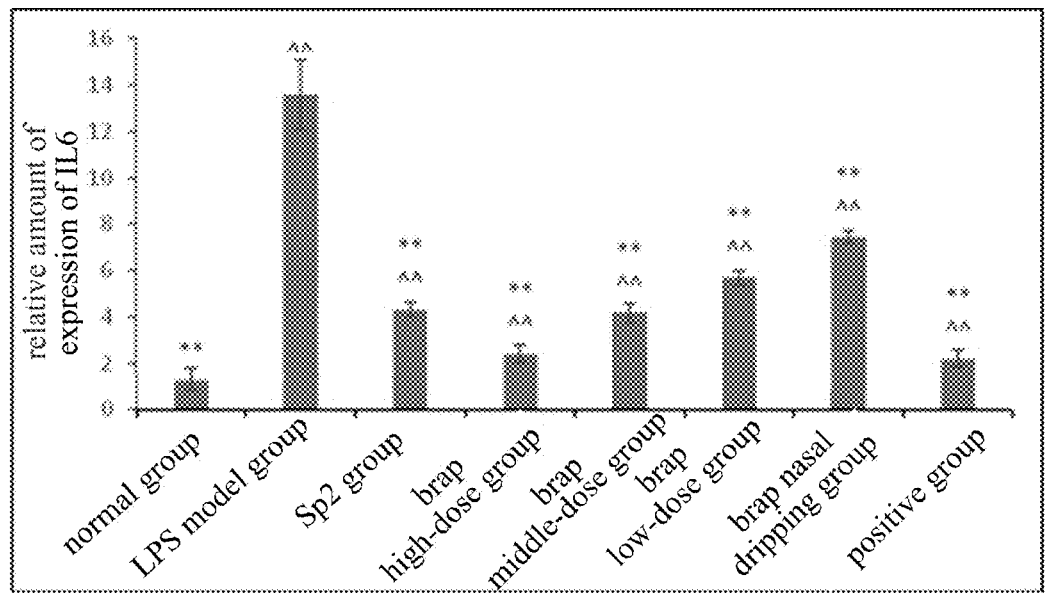
FIG. 11 shows that brap obviously decreases the overexpression of LPS-induced IL-6 mRNA in lung tissue.
Figure 12A:
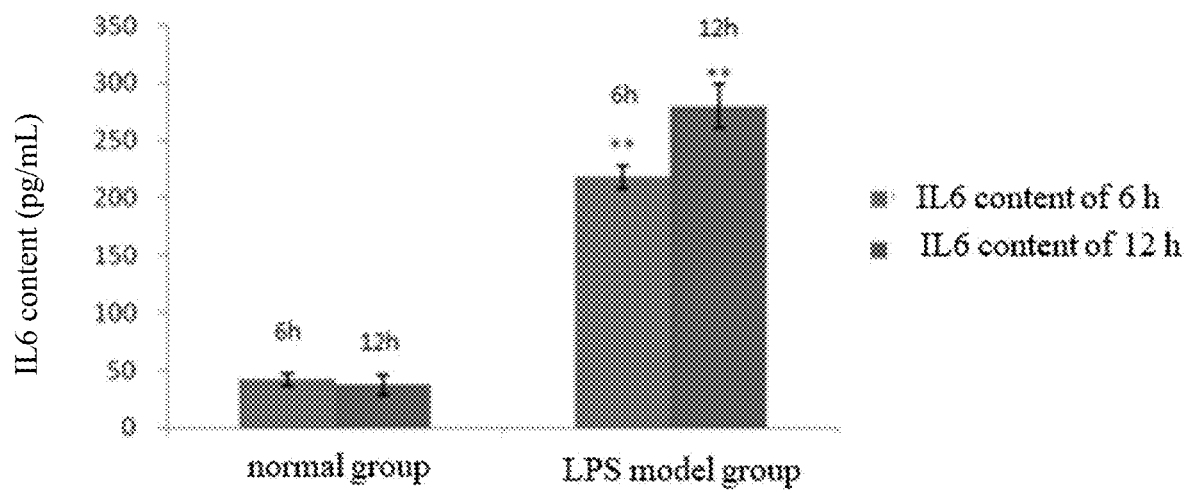
FIGS. 12A-12C show that brap obviously decreases the increase of the LPS-induced IL-6 level in blood.
Figure 12B:
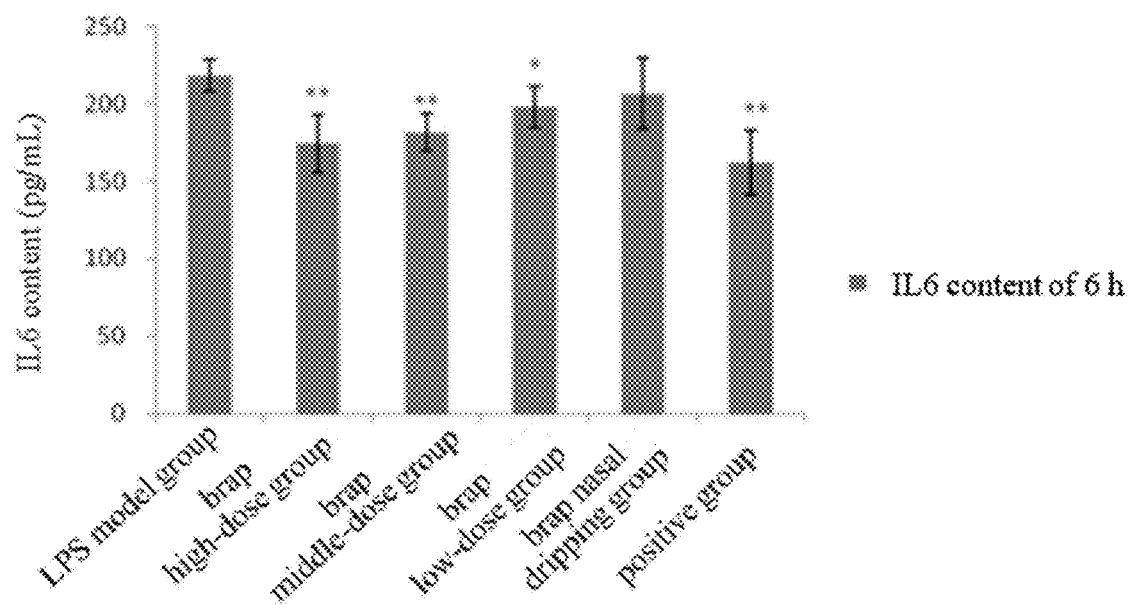
Figure 12C:
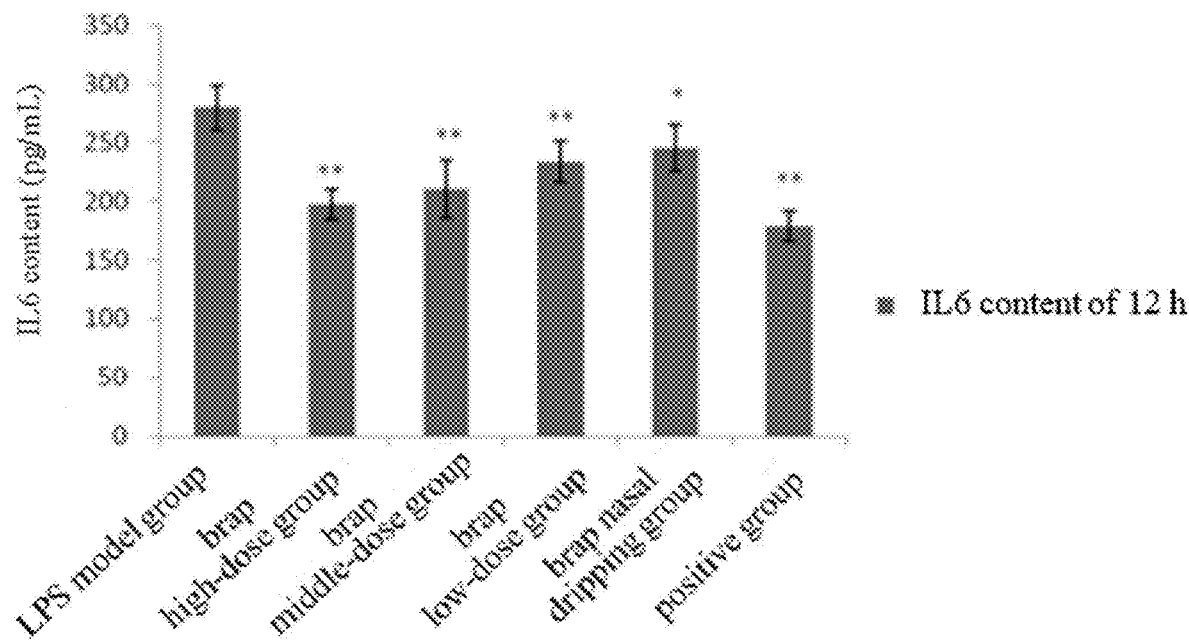
Figure 13A:
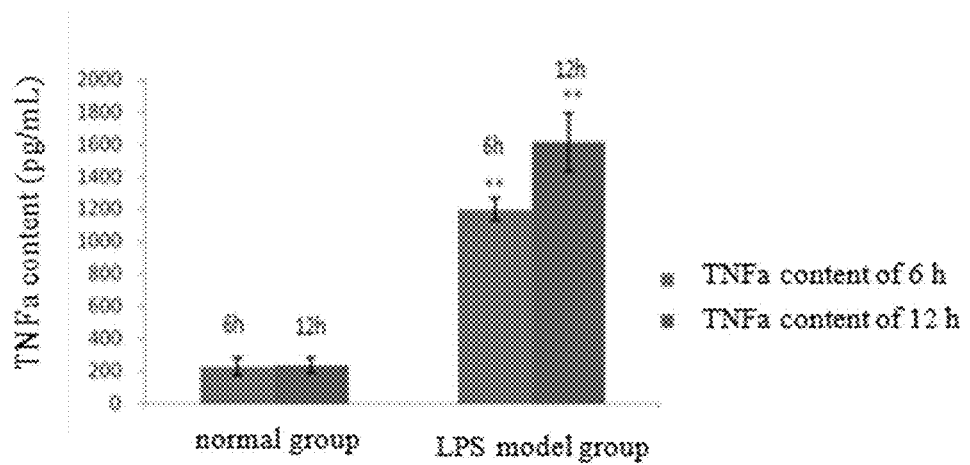
FIGS. 13A-13C show that brap obviously decreases the increase of TNF-α in the blood induced by LPS.
Figure 13B:
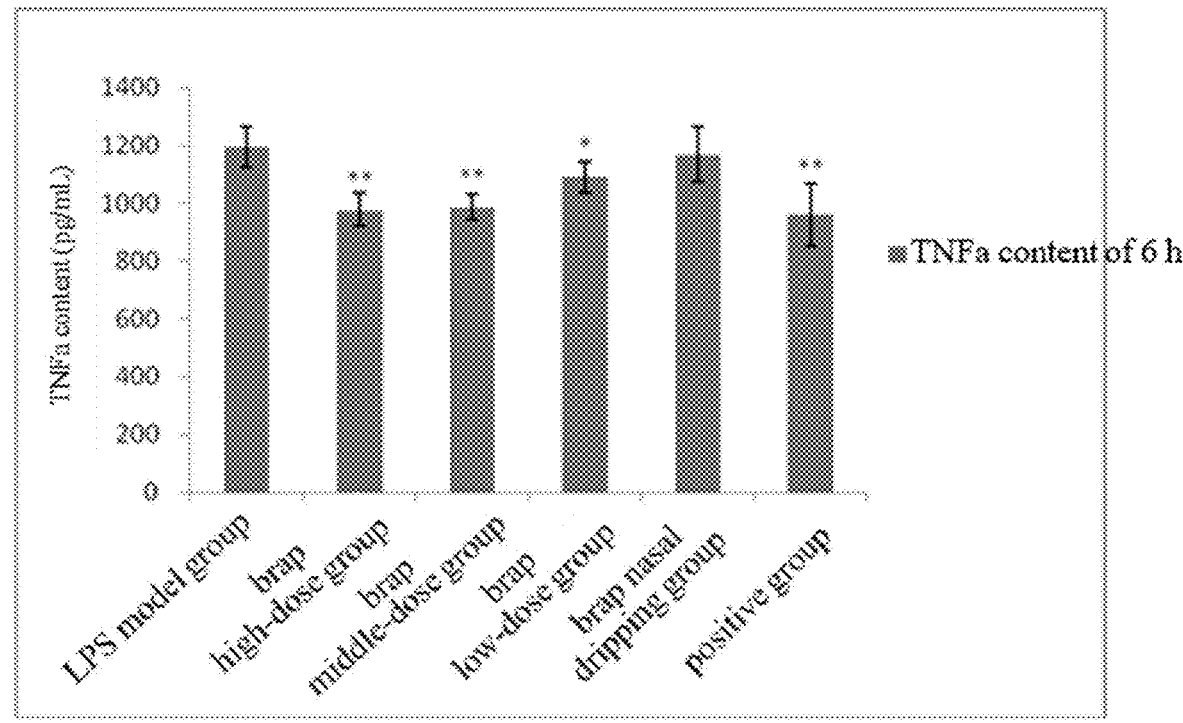
Figure 13C:
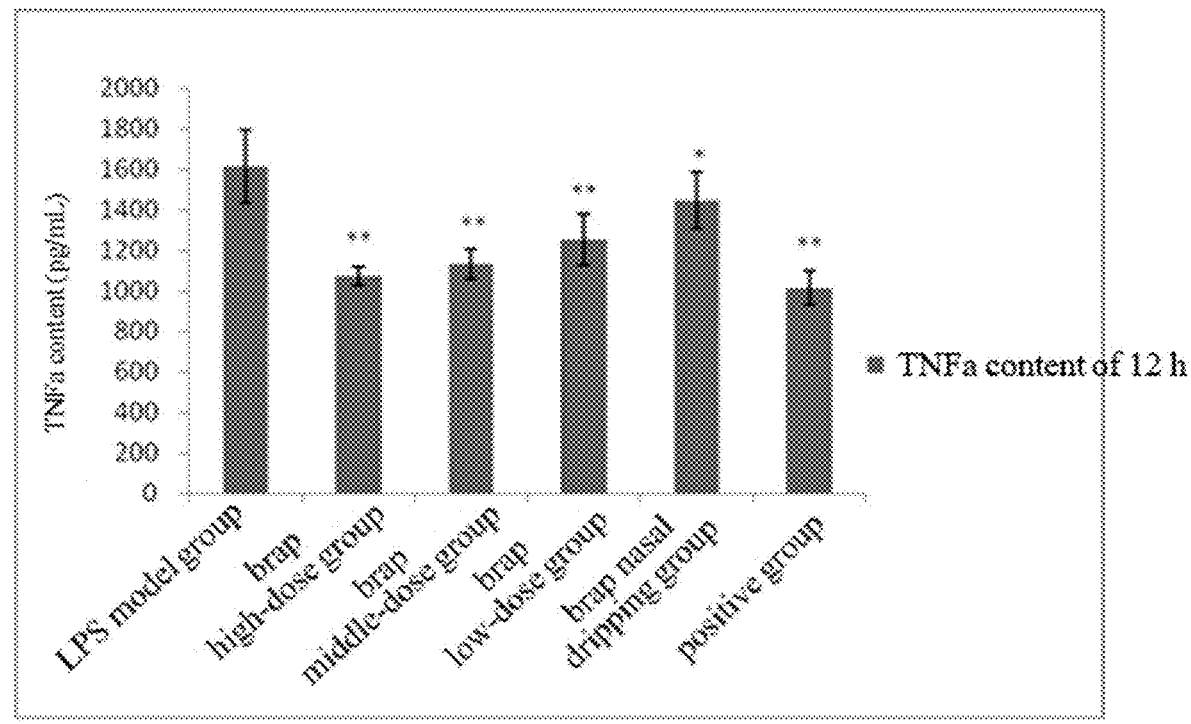

Experimental results were as shown in FIG. 11, and the results show that either intravenous injection or intranasal administration of the synthetic peptide brap can obviously decrease the overexpression of the IL-6 mRNA in LPS-induced mice lung issues.

Example 12 Detection of Cytokine Content in Blood Serum

Reagent

| Reagent | Manufacturers | Item No. |
|---|---|---|
| Mouse TNFa elisa kit | MEXN | M0047 |
| Mouse IL6 elisa kit | MEXN | M0042 |

Experimental Steps

1. A reagent was taken out of a kit and balanced for 30 min at room temperature;

2. standard wells and sample wells were set, and 50 ul standards at different concentrations were respectively added to each standard well.

3. 50 ul sample to be tested (blood sample from each group of mice model constructed in example 9) was first added to the wells of the sample to be tested;

4. 100 ul HRP-labeled detection antibody was respectively added to each standard well and well to be tested;

5. reaction wells were sealed by a microplate membrane for incubation for 60 min at 37° C.;

6. liquid was discarded, water was dried by an absorbent paper, each well was filled with scrubbing solution, standing for 1 min;

7. a culture solution was discarded, water was dried by an absorbent paper, and steps 2-6 were operated repeatedly for 5 times;

8. 50 ul substrate A/B was respectively added to each well for incubation for 15 min at 37° C.;

9. 50 ul stop buffer was added to each well to detect an OD value at 450 nm by an microplate reader within 15 min.

Experimental results were as shown in FIGS. 12A-12C and 13A-13C:

1. Compared with the normal group, TNF-a and IL-6 level in the LPS (5 mg/kg BW, intraperitoneal injection)-induced mice serum enhance significantly, and there is significance of difference (** denotes $p<0.01$);

2. compared with the model group, there is a dose-response relationship (^denotes $p<0.01$) in the TNF-a and IL-6 level in serum of low, medium and high-dose brap intravenous injection groups; brap nasal dripping group can decrease the TNF-a and IL-6 level in LPS-induced blood at 12 h, P<0.05.

Example 13 Detection of ROS Fluorescence Intensity in Each Lung Tissue by a Flow Cytometry Experimental Steps 1. About 100 mg fresh left lung tissue from each group of mice constructed in example 9 was taken and washed for three times with PBS to remove blood;
2. the tissue was put in a nylon net, ground by a grinding rod, and washed by PBS;
3. a cell suspension was collected, and filtered by a 200-mesh sieve to remove tissue blocks;
4. the cell suspension was collected and centrifuged for 5 min at 1000 rpm/min;
5. cellular supernatant was removed and PBS was added for resuspending;
6. 10 µmol/L DCFH-DA was prepared with a serum-free culture solution;
7. cells were centrifuged to remove PBS, and the above probe diluent was added to make the cell concentration being $10^6$/ml;
8. the cells were incubated for 30 min at 37° C., and shaken off for once every 3 min;
9. the cells were centrifuged for 5 min at 1000 rpm/min, and cell precipitates were resuspended on a serum-free culture medium;
10. step 9 was repeated for twice;
11. 500 µL PBS was added to resuspend cells, and flow cytometry was used to detect mean fluorescence intensity.

Figure 14A:
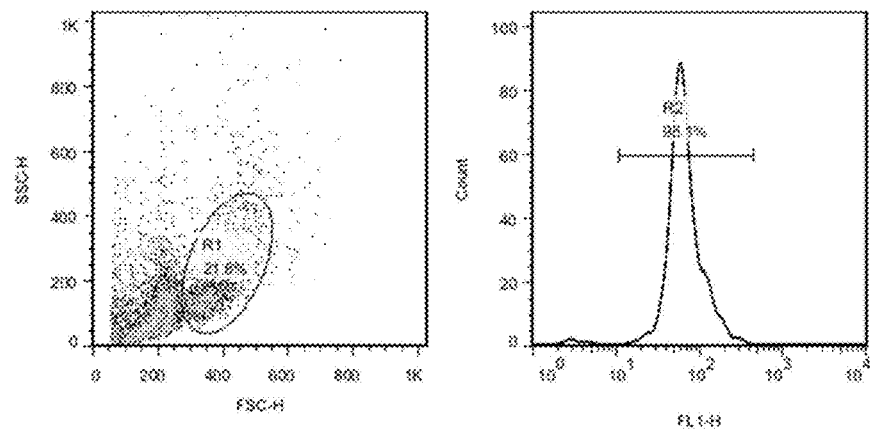
FIGS. 14A-14G show a qualitative analysis of brap obviously reducing the increase in ROS content in lung tissues induced by LPS for 6 h.
Figure 14B:
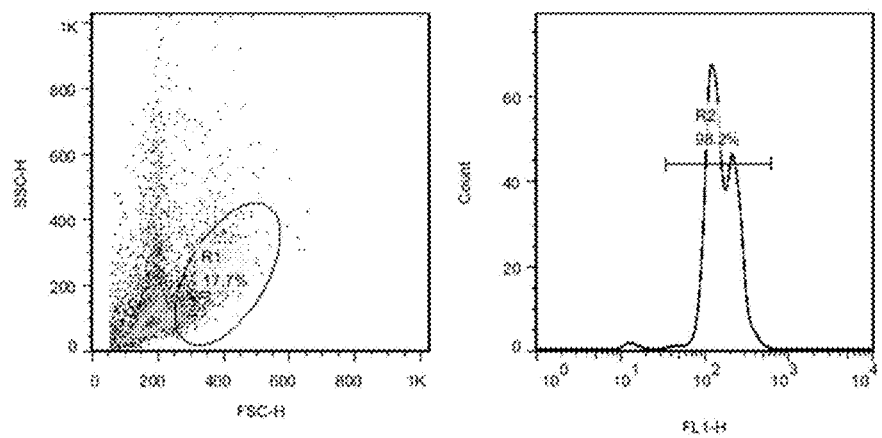
Figure 14C:
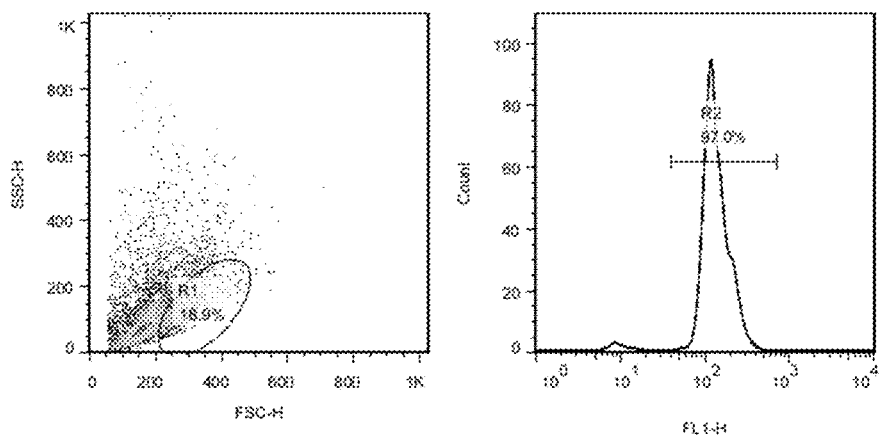
Figure 14D:
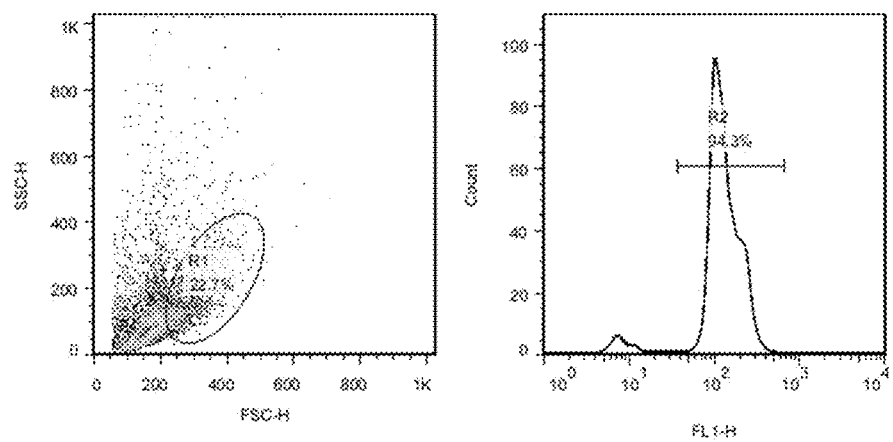
Figure 14E:
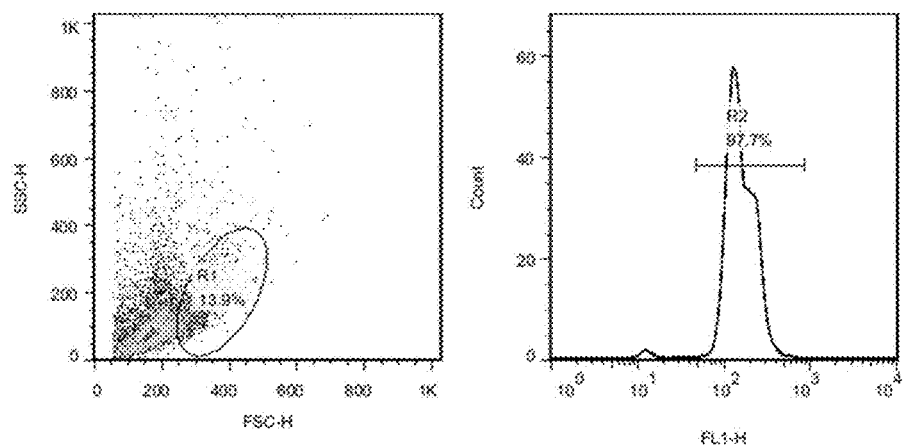
Figure 14F:
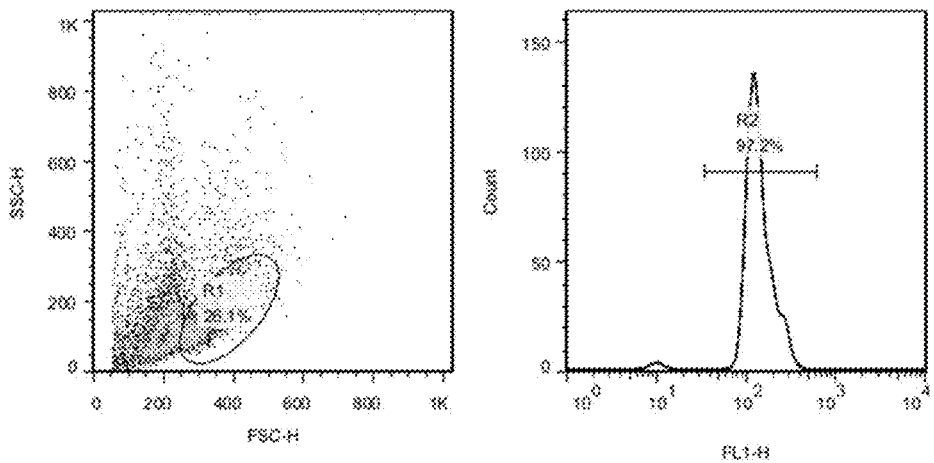
Figure 14G:
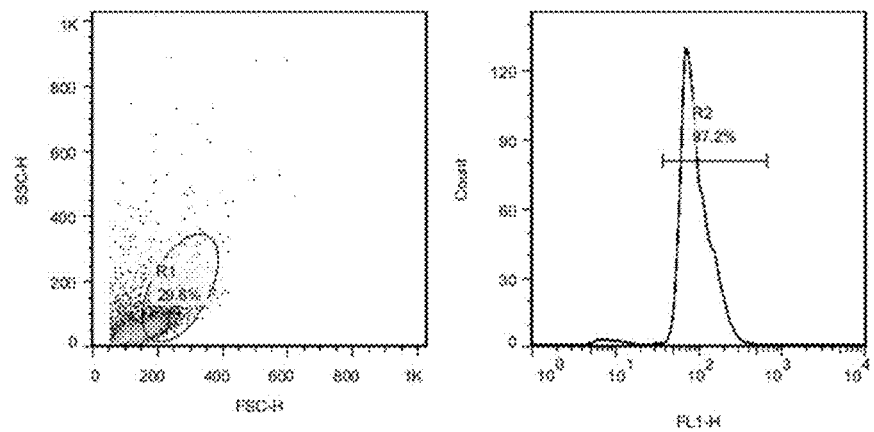

Experimental results were as shown in FIGS. 14A-14G, and FIG. 14A denotes a normal control group, FIG. 14B denotes an LPS model group (5 mg/kg BW, intraperitoneal injection); FIG. 14C denotes LPS+16 mg/kg BW synthetic peptide brap, FIG. 14D denotes LPS+8 mg/kg BW synthetic peptide brap, FIG. 14E denotes LPS+4 mg/kg BW synthetic peptide brap; FIG. 14F denotes LPS+synthetic peptide brap (intranasal injection on both sides for 15 µL/side/day); and FIG. 14G denotes a positive control group (LPS+dexamethasone 5 mg/kg, intraperitoneal injection).

Figure 15:
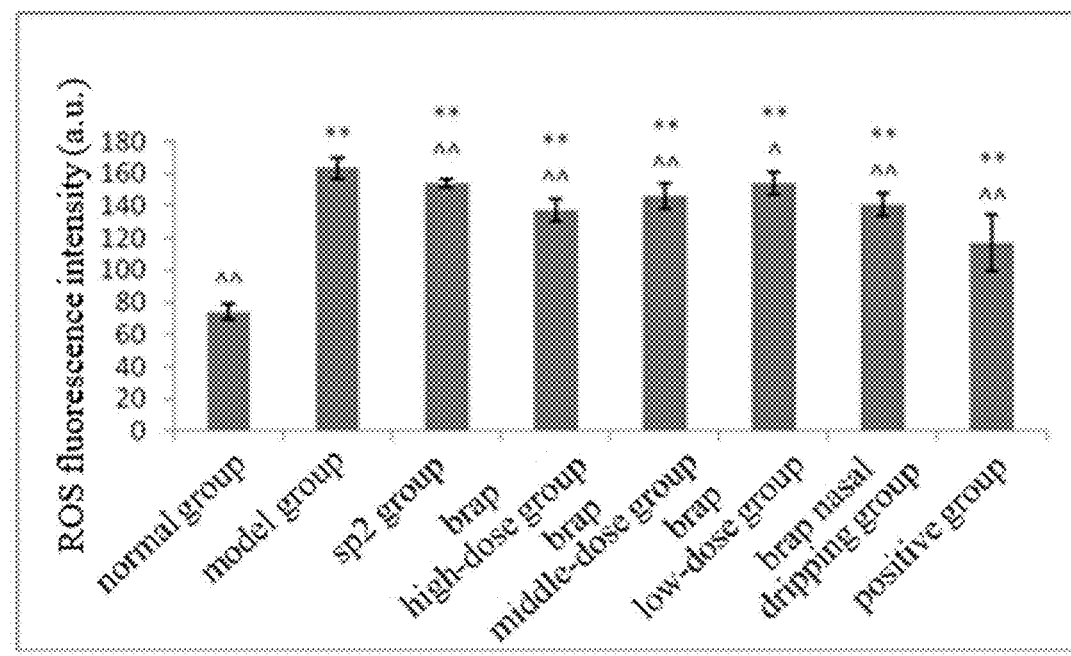
FIG. 15 is a qualitative analysis of brap obviously reducing the increase in ROS content in lung tissue induced by LPS for 12 h.

FIG. 15 denotes detection of ROS mean fluorescence intensity in each group of mice lung tissue by a flow cytometry Example 14 Limit Test on Intravenous Injection of Brap with 2000 mg/kg BW Dose Level The technique was provided by Shanghai Meixuan Biological Science and Technology Co., Ltd.

I. Test Animal (Subject): Konmin Mouse: Healthy, Adult, Male, Weight≤20 g, and n=5 pcs II. Test Sample: Synthetic Peptide Brap 1. Lot No.: 04010039572, and synthesized by China Peptides Co., Ltd.
2. Content: The sample was sub-packaged accurately into 5 mg/bottle×8 bottles (for the first mouse), and 8 mg/bottle× 20 bottles (for the other 4 mice), and not weighed any more;
3. Storage condition: The sample was kept at −20° C.;
4. Sample purity: Purity was detected >99.49% by HPLC.
5. Preparation method: a synthetic peptide freeze-dried powder was taken out at −20° C., and put for recovery at room temperature, and then 1.5 ml normal saline was added for oscillation to be dissolved fully.

III. Administration Route and Dose: 2000 mg/kg BW was Injected Via a Tail Vein

IV. Administration Mode

Administration capacity: the maximum injection capacity of the mice tail vein was 0.5 ml/once, slow injection
Dose and mode of administration: 40 mg/1.5 ml working solution was administered for 3 times within 9 h.

V. Experimental Steps 1) a test substance (synthetic peptide brap) having a dose of 2000 mg/kg was injected to the first Konmin mouse via tail vein;
2) whether of causing toxic responses (initial symptom, starting time, namely, time period after administration, severity and duration) was observed and recorded;
3) if the animal died, the response before being at death's door and the occurrence time of death were recorded.

TABLE 2

Limit test on intravenous injection of the synthetic peptide brap with a 2000 mg/kg BW dose level

| Animal No. | Animal Body weight (g) | The volume (ml) of the synthetic peptide brap was calculated by mice body weight: Dose: 2000 mg/kg BW, Dissolving by 40 mg/1.5 ml/20 g BW, The administration volume as calculated by body weight: The administration volume per day (ml) = 0.075 ml/g * body weight (g) | Times of administration Administration for 3 times within 24 h (at intervals of 3-4 h); | Toxic response manifestation Occurrence time of the symptoms: Severity: Duration: | Death situation/survival animals Response before reaction: Occurrence time of death after administration: 72 h after administering the survival animals: |
|---|---|---|---|---|---|
| 1 | 19.4 g | 5 mg*8 bottles were diluted to 1.5 ml. Injection 3 times for 1.455 ml, and 0.485 ml/times. | At 9:00, 13:00 and 16:00 | No abnormal response | No death |

TABLE 2-continued

Limit test on intravenous injection of the synthetic peptide brap with a 2000 mg/kg BW dose level

| Animal No. | Animal Body weight (g) | The volume (ml) of the synthetic peptide brap was calculated by mice body weight: Dose: 2000 mg/kg BW, Dissolving by 40 mg/1.5 ml/20 g BW, The administration volume as calculated by body weight: The administration volume per day (ml) = 0.075 ml/g * body weight (g) | Times of administration Administration for 3 times within 24 h (at intervals of 3-4 h); | Toxic response manifestation Occurrence time of the symptoms: Severity: Duration: | Death situation/survival animals Response before reaction: Occurrence time of death after administration: 72 h after administering the survival animals: |
|---|---|---|---|---|---|
| 2 | 20.3 g | 8 mg*8 bottles were diluted to 6 ml. Injection 3 times for 1.523 ml, and 0.508 ml/times. | At 9:00, 13:00 and 16:00 | No abnormal response | No death |
| 3 | 20.5 g | 8 mg*20 bottles were diluted to 6 ml. Injection 3 times for 1.538 ml, and 0.513 ml/times. | At 9:00, 13:00 and 16:00 | No abnormal response | No death |
| 4 | 20.0 g | 8 mg*20 bottles were diluted to 6 ml. Injection 3 times for 1.50 ml, and 0.50 ml/times. | At 9:00, 13:00 and 16:00 | No abnormal response | No death |
| 5 | 19.7 g | 8 mg*20 bottles were diluted to 6 ml. Injection 3 times for 1.50 ml, and 0.50 ml/times. | At 9:00, 13:00 and 16:00 | No abnormal response | No death |

Result judgment: if the number of the survival animals is ≥3, LD50 is greater than 2000 mg/kg.

Conclusion: no toxicity was found in the limit test on the intravenous injection of 2000 mg/kg BW dose level.

The invention claimed is:

1. A synthetic bradykinin receptor antagonism peptide (brap), comprising the amino acid sequence of SEQ ID NO: 1.

2. A pharmaceutical composition comprising the synthetic brap according to claim 1.

3. A method of inhibiting G-protein-coupled bradykinin (BK) B1 and B2 receptors in a subject in need thereof, comprising administering to the subject an effective amount of a composition, wherein the composition comprises the synthetic brap according to claim 1.

4. The method according to claim 3, wherein the composition is administered intravenously or intranasally.

5. A method of treating acute lung injury in a subject in need thereof, comprising administering to the subject an effective amount of a composition, wherein the composition comprises the synthetic brap according to claim 1.

6. The method according to claim 5, wherein the composition is administered intravenously or intranasally.

7. A method of treating COVID-19 inflammation in a subject in need thereof, comprising administering to the subject an effective amount of a composition, wherein the composition comprises the synthetic brap according to claim 1.

8. The method according to claim 7, wherein the composition is administered intravenously or intranasally.

9. A method of treating allergic rhinitis in a subject in need thereof, comprising administering to the subject an effective amount of a composition, wherein the composition comprises the synthetic brap according to claim 1.

10. The method according to claim 9, wherein the composition is administered intravenously or intranasally.

* * * * *